United States Patent
Delagrave et al.

(10) Patent No.: US 11,286,465 B2
(45) Date of Patent: Mar. 29, 2022

(54) ICP0-MEDIATED ENHANCED EXPRESSION SYSTEM

(71) Applicant: Sanofi Pasteur Biologies, LLC, Cambridge, MA (US)

(72) Inventors: Simon Delagrave, Cambridge, MA (US); CharChang Lai, Cambridge, MA (US)

(73) Assignee: SANOFI PASTEUR INC., Swiftwater, PA (US)

( * ) Notice: Subject to any disclaimer, the term of this patent is extended or adjusted under 35 U.S.C. 154(b) by 38 days.

(21) Appl. No.: 16/230,990

(22) Filed: Dec. 21, 2018

(65) Prior Publication Data
US 2019/0194626 A1  Jun. 27, 2019

Related U.S. Application Data

(63) Continuation of application No. 15/572,890, filed as application No. PCT/US2016/032082 on May 12, 2016, now Pat. No. 10,208,292.

(60) Provisional application No. 62/161,194, filed on May 13, 2015.

(51) Int. Cl.
C12N 7/00 (2006.01)

(52) U.S. Cl.
CPC ...... C12N 7/00 (2013.01); *C12N 2710/16622* (2013.01); *C12N 2710/16634* (2013.01); *C12N 2710/16651* (2013.01)

(58) Field of Classification Search
CPC .. A61K 2300/00; A61K 39/12; A61K 35/763; A61K 39/245; A61K 2039/5254; A61K 35/76; A61K 2039/525; C12N 7/00; C12N 15/86; C12N 2710/16643; C12N 2710/16634; C12N 2710/16034; C12N 2710/16611; C12N 2710/16651; C12N 15/869; C12N 2710/16652; C12N 2710/16661; C07K 14/005; C07K 14/035
See application file for complete search history.

(56) References Cited

U.S. PATENT DOCUMENTS

| | | | | |
|---|---|---|---|---|
| 5,686,601 A | * | 11/1997 | Weber | C07K 14/005 536/23.1 |
| 5,804,413 A | * | 9/1998 | DeLuca | C12N 7/00 435/235.1 |
| 6,261,552 B1 | * | 7/2001 | DeLuca | C07K 14/005 424/93.2 |
| 2016/0153000 A1 | | 6/2016 | Glorioso et al. | |
| 2020/0172928 A1 | * | 6/2020 | Yao | C12N 15/86 |

FOREIGN PATENT DOCUMENTS

WO  WO 2013/106398 A1  7/2013
WO  WO 2016/183312 A1  11/2016

OTHER PUBLICATIONS

Smith MC, Boutell C, Davido DJ. HSV-1 ICP0: paving the way for viral replication. Future Virol. Apr. 2011;6(4):421-429.*
Hobbs WE, Brough DE, Kovesdi I, DeLuca NA. Efficient activation of viral genomes by levels of herpes simplex virus ICP0 insufficient to affect cellular gene expression or cell survival. J Virol. Apr. 2001;75(7):3391-403.*
Wu N, Watkins SC, Schaffer PA, DeLuca NA. Prolonged gene expression and cell survival after infection by a herpes simplex virus mutant defective in the immediate-early genes encoding ICP4, ICP27, and ICP22. J Virol. Sep. 1996;70(9):6358-69.*
Sekulovich RE, Leary K, Sandri-Goldin RM. The herpes simplex virus type 1 alpha protein ICP27 can act as a trans-repressor or a trans-activator in combination with ICP4 and ICP0. J Virol. Dec. 1988;62(12):4510-22.*
Hagglund R, Roizman B. Role of ICP0 in thestrategy of conquest of the host cell by herpes simplex virus 1. J Virol. Mar. 2004;78(5):2169-78.*
Mosca JD, et al. Activation of human immunodeficiency virus by herpesvirus infection: identification of a region within the long terminal repeat that responds to a trans-acting factor encoded by herpes simplex virus 1. Proc Natl Acad Sci U S A. Nov. 1987;84(21)7408-12.*
Ostrove JM, Leonard J, Week KE, Rabson AB, Gendelman HE. Activation of the human immunodeficiency virus by herpes simplex virus type 1. J Virol. Dec. 1987;61(12):3726-32.*
Everett RD, Parsy ML, Orr A. Analysis of the functions of herpes simplex virus type 1 regulatory protein ICP0 that are critical for lytic infection and derepression of quiescent viral genomes. J Virol. May 2009;83(10):4963-77. Epub Mar. 4, 2009.*
Everett RD, Orr A. Herpes simplex virus type 1 regulatory protein ICP0 aids infection in cells with a preinduced interferon response but does not impede interferon-induced gene induction. J Virol. May 2009;83(10):4978-83. Epub Mar. 4, 2009.*
Paladino P, Collins SE, Mossman KL. Cellular localization of the herpes simplex virus ICP0 protein dictates its ability to block IRF3-mediated innate immune responses. PLoS One. Apr. 29, 2010;5(4):e10428.*
Cuchet D, Ferrera R, Lomonte P, Epstein AL. Characterization of antiproliferative and cytotoxic properties of the HSV-1 immediate-early ICP0 protein. J Gene Med. Sep. 2005;7(9):1187-99.*
Gius D, Laimins LA. Activation of human papillomavirus type 18 gene expression by herpes simplex virus type 1 viral transactivators and a phorbol ester. J Virol. Feb. 1989;63(2):555-63.*

(Continued)

*Primary Examiner* — Rachel B Gill
(74) *Attorney, Agent, or Firm* — McNeill Baur PLLC

(57) ABSTRACT

Methods and compositions for increasing the production of recombinant proteins by introducing ICP0 to cells capable of producing a recombinant protein are encompassed. In one method, the recombinant protein is a protein that is required for the replication of a replication defective virus, wherein the recombinant protein is provided to the replication defective virus in trans.

7 Claims, 17 Drawing Sheets

Specification includes a Sequence Listing.

(56) References Cited

OTHER PUBLICATIONS

Kuroda S, Miyagawa Y, Sato Y, Yamamoto M, Adachi K, Kinoh H, Goins WF, Cohen JB, et al. Protocol Optimization for the Production of the Non-Cytotoxic JΔNI5 HSV Vector Deficient in Expression of Immediately Early Genes. Mol Ther Methods Clin Dev. Mar. 17, 2020;17:612-621. (Year: 2020).*

Azizi et al., "Determination of HSV-1 UL5 and UL29 gene copy numbers in an HSV complementing Vero cell line," J Biotechnol 168, 382 (Dec. 2013).

Barlow, "Structure of the $C_3HC_4$Domain by $^1$H-nuclear Magnetic Resonance Spectroscopy. A New Structural Class of Zinc-finger" J. Mol. Biol. 237, 201-211 (1994).

Belshe et al., "Efficacy Results of a Trial of a Herpes Simplex Vaccine," The New England Journal of Medicine, 366: 34-43 (2012).

Bernard et al., "Immunogenicity, Protective Efficacy, and Non-Replicative Status of the HSV-2 Vaccine Candidate HSV529 in Mice and Guinea Pigs," PLOS One 10(4): e0121518, 21 pages (2015).

Boehmer et al., "Association of Origin Binding Protein and Single Strand DNA-binding Protein, ICP8, during Herpes Simplex Virus Type 1 DNA Replication in Vivo," Journal of Biological Chemistry 269(46): 29329-29334 (1994).

Boutell and Davido, "A quantitative assay to monitor HSV-1 ICP0 ubiquitin ligase activity in vitro," Methods, (90) 3-7(2015).

Boutell et al. "Herpes Simplex Virus Type 1 Immediate-Early Protein ICP0 and Its Isolated RING Finger Domain Act as Ubiquitin E3 Ligases In Vitro," Journal of Virology. 76(2):841-850 (Jan. 2002).

Boutell et al. Regulation of alphaherpesvirus infections by the ICP0 family of proteins. J Gen Virol., 94(Pt 3): 465-481 (2013).

Cai et al. "Herpes simplex virus type 1 ICP0 regulates expression of immediate-early, early, and late genes in productively infected cells," J. Viral. 66(5): 2904-2915 (1992).

Cai et al., "Herpes simplex virus type 1 ICP0 plays a critical role in the de nova synthesis of infectious virus following transfection of viral DNA," J. Viral., 63(11): 4579-4589 (1989).

Da Costa et al. "Construction, Phenotypic Analysis, and Immunogenicity of a UL5/UL29 Double Deletion Mutant of Herpes Simplex Virus 2," Journal of Virology pp. 7963-7971 (2000).

Davido et al. "Analysis of the basal and inducible activities of the ICP0 promoter of herpes simplex virus type 1," J. Gen. Virol., 79: 2093-2098 (1998).

Delagrave et al. "Immunogenicity and efficacy of intramuscular replication-defective and subunit vaccines against herpes simplex virus type 2 in the mouse genital model." PLoS One: 7(10): e46714 (2012).

Dudek and Knipe "Replication-defective viruses as vaccines and vaccine vectors," Virology 344(1): 230-239 (2006).

Everett et al. "Comparison of the Biological and Biochemical Activities of Several Members of the Alphaherpesvirus ICP0 Family of Proteins," Journal of Virology, 84(7): 3476-3487 (Apr. 2010).

International Search Report and Written Opinion for application No. PCT/US2016/032082, 14 pages (dated Jul. 19, 2016).

Jordan et al. "Activation of Gene Expression by Herpes Simplex Virus Type 1 ICP0 Occurs at the Level of MRNA Synthesis," Journal of Virology pp. 6850-6862 (Sep. 1997).

Lanfranca et al., "ESV-1 ICP0: An E3 Ubiquitin Ligase That Counteracts Host Intrinsic and Innate Immunity," Cells 3: 438-454 (2014).

Mundle et al. "High-purity preparation of HSV-2 vaccine candidate ACAM529 is immunogenic and efficacious in vivo," PLoS One, 8(2): e57224. (Epub Feb. 26, 2013).

Petrakova et al., "Noncytopathic Replication of Venezuelan Equine Encephalitis Virus and Eastern Equine Encephalitis Virus Replicons in Mammalian Cells," Journal of Virology, 79(12): 7597-7608 (Jun. 2005).

Quinlan et al. "Stimulation of Expression of a Herpes Simplex Virus DNA-Binding Protein by Two Viral Functions," Molecular and Cellular Biology 5(5): 957-963 (1985).

Samaniego et al. "The herpes simplex virus immediate-early protein ICP0 affects transcription from the viral genome and infected-cell survival in the absence of ICP4 and ICP27," J. Virol., 71 (6): 4614-4625 (1997).

Yao "An activity specified by the osteosarcoma line USOS can substitute functionally for ICP0, a major regulatory protein of herpes simplex virus type 1," Journal of Virology, 69(10): 6249-6258 (1995).

Prosecution History of U.S. Appl. No. 15/572,890, 35 U.S.C. § 371(c) date Nov. 9, 2017.

* cited by examiner

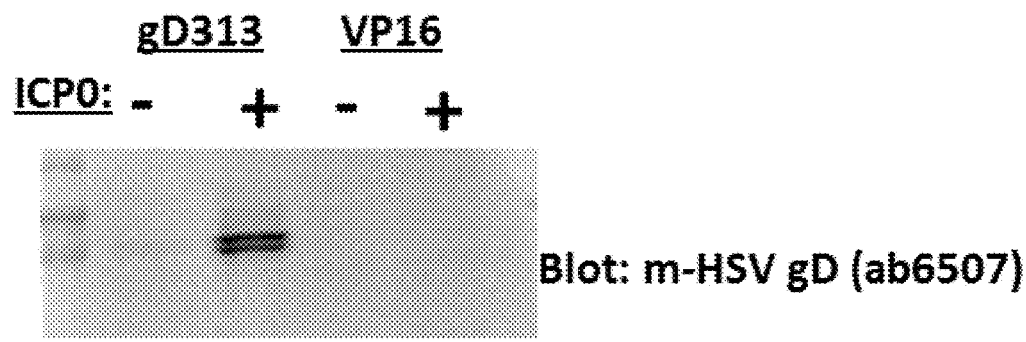
*FIG. 8A*
*FIG. 8B*
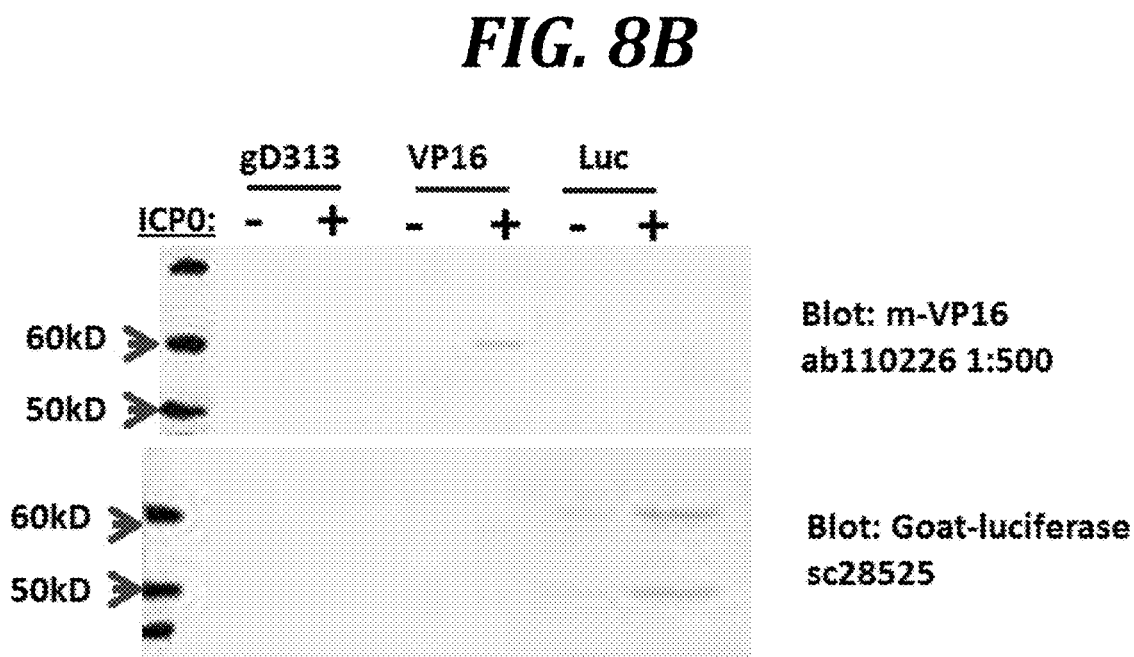

ICP0-MEDIATED ENHANCED EXPRESSION SYSTEM

CROSS REFERENCE TO RELATED APPLICATIONS

This application is a continuation application of U.S. application Ser. No. 15/572,890, the 35 U.S.C. 371(c) date of which is Nov. 9, 2017, which is a national phase entry pursuant to 35 U.S.C. 371 of International Application No. PCT/US2016/032082, filed May 12, 2016, which claims the benefit of priority of US Provisional Application No. 62/161,194, filed May 13, 2015, all of which are incorporated by reference in their entireties for any purpose.

SEQUENCE LISTING

The present application is filed with a Sequence Listing in electronic format. The Sequence Listing is provided as a file entitled "2018-12-17_01121-0005-01US_ST25" created on Dec. 17, 2018, which is 20.2 KB in size. The information in the electronic format of the sequence listing is incorporated herein by reference in its entirety.

FIELD

Methods and compositions for enhancing expression of recombinant proteins are provided.

BACKGROUND

The efficient expression of recombinant proteins is essential for production of therapeutic proteins, particularly when the protein is partially toxic to the host cell producing it. Efficient expression is also vital when producing replication defective virus for use in vaccines. In this scenario, certain essential genes are removed from the viral genome to prevent viral replication in the vaccine. However, in order to grow the vaccine virus in cell culture, the proteins required for replication of the virus may be provided in trans to complement the replication defective virus, and suboptimal expression of these complementary proteins may limit viral yield.

Genital herpes is a sexually transmitted disease usually caused by infection with herpes simplex virus type 2 (HSV-2). After infection, HSV-2 can persist with latent virus in the neural ganglia, allowing episodic outbreaks of painful genital lesions in up to 25% of patients who are infected. Transmission of HSV from an infected woman with active disease to her newborn can also lead to severe neurologic complications or death in the baby.

The life cycle of HSV can be divided into lytic infection of keratinocytes and fibroblasts and latent infection of sensory neurons. During HSV's latent stage, its genome remains quiescent with few or no genes expressed. External stressors may activate HSV's lytic phase, where a full program of gene expression and genome replication is activated yielding new virions.

As with many viruses, HSV genes can be divided into three broad categories, called immediate early (IE), early (E), and late (L), depending on the timing of their expression after infection. Herpes simplex virus infected cell polypeptide zero ("ICP0") is an IE protein found in HSV and related alphaherpesviruses. ICP0 was discovered in the late 1980s and early 1990s, but its function is still largely unknown. It has been reported that ICP0 may activate gene transcription, and deletion of ICP0 reduces HSV replication in vitro and attenuates the virus in vivo by inactivating its ability to transition to lytic replication. See, e.g., Boutell and Everett, J. Gen. Virol (2013) 94:465-481, and Lanfranca et al., Cells (2014) 3:438-454.

At the molecular level, ICP0 has a highly complex phenotype. At least four mechanisms have been proposed to explain how ICP0 modulates gene transcription. These generally involve the modification of chromatin in order to derepress the HSV genome after replication in neuronal cells. ICP0 has also been proposed to interact with transcription factor E2FBP1. In addition, a fundamental feature of ICP0 is its E3 ubiquitin ligase activity mediated by its RING domain. ICP0 causes ubiquitination of proteins, which leads to their degradation or changes in their function. A number of proteins targeted for ubiquitination by ICP0 participate in mechanisms through which cells resist viral infections. For example, PML, a component of the ND10 nuclear bodies, which interfere with HSV genome replication, is degraded by ICP0-mediated ubiquitination, as are other proteins such as IFI16 and IkBa involved in innate immunity to infections. Despite the apparent importance of ICP0 in HSV life cycle, very little is known about ICP0.

Development of an HSV-2 vaccine may be able to prevent herpes disease and block spread of the virus. Previous clinical studies of an HSV-2 subunit vaccine containing glycoprotein D, however, failed to show efficacy at preventing HSV-2 infection, see R. B. Belshe et al., NEJM 366:34-43 (2012). It has been proposed that a vaccine capable of mimicking natural viral infection and inducing a broad immune response may be an attractive vaccine candidate, as noted in M. C. Bernard et al., PLOS One 10(4):e0121518 (2015).

HSV529 is a replication defective HSV-2 variant, also known as ACAM529, as described in Delagrave et al., PLOS One 7(10):e46714 (2012), and M. C. Bernard et al., PLOS One 10(4):e0121518 (2015). The HSV529 virus, which is a plaque-purified clone of the re-derived strain d15-29 lacks two viral DNA replication genes ($U_L5$ and $U_L29$) and cannot replicate in the absence of these gene products. Da Costa et al. J. Virol. 7963-7971 (2000); S. T. Mundle, PLOS One 8(2):e57224 (2013). The HSV529 virus is grown using the complementary helper cell line, AV529-19, which is a Vero cell line that was stably transfected to supply UL5 and UL29 HSV-2 proteins in trans in infected cells. In mouse and guinea pig models of genital herpes, HSV529 induces immune responses and blocks HSV-2 infection, see M. C. Bernard et al., PLOS One 10(4):e0121518 (2015) and references therein.

We herein describe that the wild-type HSV-2 virus generates significantly higher virus yield than the HSV529 after infection of AV529-19 cells. Given the need to generate the HSV529 clinical candidate at a large scale for clinical purposes, we investigated methods to increase viral yield. Given the known critical role of ICP8 (the protein expressed by the UL29 gene) in HSV-2 replication, see P. E. Boehmer et al., J Biol Chem 269(46):29329-3 (1994), we investigated expression of ICP8 in AV529-19 cells. We unexpectedly found that ICP8 could only be detected in AV529-19 cells after infection with HSV529. Thus, there exists a need in the art to improve recombinant protein production in AV529-19 cells to increase the yield of HSV529 production. There is also a need in the art to increase protein production in other systems, such as, for example, when producing therapeutic biologics for mass production, and when producing replication defective vaccine in trans complementary systems.

SUMMARY

In evaluating the means by which ICP8 is increased in AV529-19 cells following HSV529 infection, we have determined that the immediate early HSV protein, ICP0, is capable of inducing AV529-19 cells to increase expression of ICP8. Delivery of recombinant ICP0, by transduction or transfection, can increase levels of ICP8, as well as being able to increase expression of recombinant proteins. In addition, expression of ICP0 in AV529-19 cells before infection with the HSV529 virus leads to significantly increased viral yields.

In accordance with the description, the inventors have achieved increased expression of proteins through co-expression of ICP0. In one embodiment, a method for increasing the yield of recombinant protein expression in vitro is encompassed, wherein ICP0 is introduced to a cell expressing a recombinant protein, thereby increasing the yield of the recombinant protein. In one embodiment the cell is AV529-19, and the recombinant protein is ICP8 or pUL5.

In one embodiment, the invention comprises a method for producing replication defective virus or viral vaccine in culture. The method comprises providing a cell comprising at least one recombinant protein, wherein this recombinant protein is required for the replication of an otherwise replication defective virus. Introduction of ICP0 to the cell is done to increase expression of the recombinant protein, the replication defective virus is introduced to the cell, and the replication defective virus or viral vaccine is isolated. The introduction of ICP0 increases the yield of the replication defective virus.

In certain embodiments, the cell is AV529-19, and the recombinant protein is ICP8 or pUL5.

In certain embodiments, the recombinant protein complements a replication defective virus in trans.

In another embodiment, the replication defective HSV-2 vaccine HSV529 is produced in AV529-19 cells after introduction of ICP0. ICP0 is introduced to AV529-19 cells, wherein ICP0 increases the expression of at least one of ICP8 or pUL5 complementing proteins. AV529-19 cells are infected with the HSV529 virus, and the HSV529 vaccine is isolated. The introduction of ICP0 increases the yield of the replication defective HSV-2 vaccine HSV529.

In certain embodiments, the nucleic acid encoding the recombinant protein is episomal or integrated into the host cell genome. This nucleic acid may be DNA or RNA.

ICP0 may be introduced to the cell by transfection or transduction. ICP0 may be introduced by transduction with HSV-2, replication defective HSV-2, HSV529, or HSV-1. ICP0 may also be introduced by transduction with an adenovirus expressing ICP0. ICP0 may be introduced by transfection with a plasmid encoding ICP0; this plasmid may have an inducible or non-inducible promoter that drives expression of ICP0. The inducible promoter may be selected from chemically- or physically-regulated promoters. Expression of ICP0 by this inducible promoter may be regulated by a small molecule, such as doxycycline. The non-inducible promoter may be selected from the group consisting of CMV and SV40 promoters, as well as those containing known promoter elements such as TATA box, GC-box, CCAAT box, B recognition element, and initiator element.

In certain embodiments, the quantity of recombinant protein produced or isolated is greater than the quantity of recombinant protein produced or isolated in control cells that do not comprise ICP0.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to explain the principles described herein.

BRIEF DESCRIPTION OF THE DRAWINGS

FIGS. 8A and 8B show that co-transduction of ICP0 increases the expression of episomally encoded recombinant proteins. AV529-19 cells were transduced with adenovirus vectors expressing gD313, VP16, or luciferase (Luc) and then 24 h later with either an empty adenovirus vector or an adenovirus expressing ICP0. Twenty-four hours after co-transduction, samples were collected for western blots.

In FIG. 9A, cell lysates were harvested 24 h post-transduction and analyzed by western blotting against the housekeeping protein GAPDH. In FIG. 9B, cell lysates were analyzed by SDS-PAGE and Simple-Blue staining.

DESCRIPTION OF THE SEQUENCES

Figure 1:
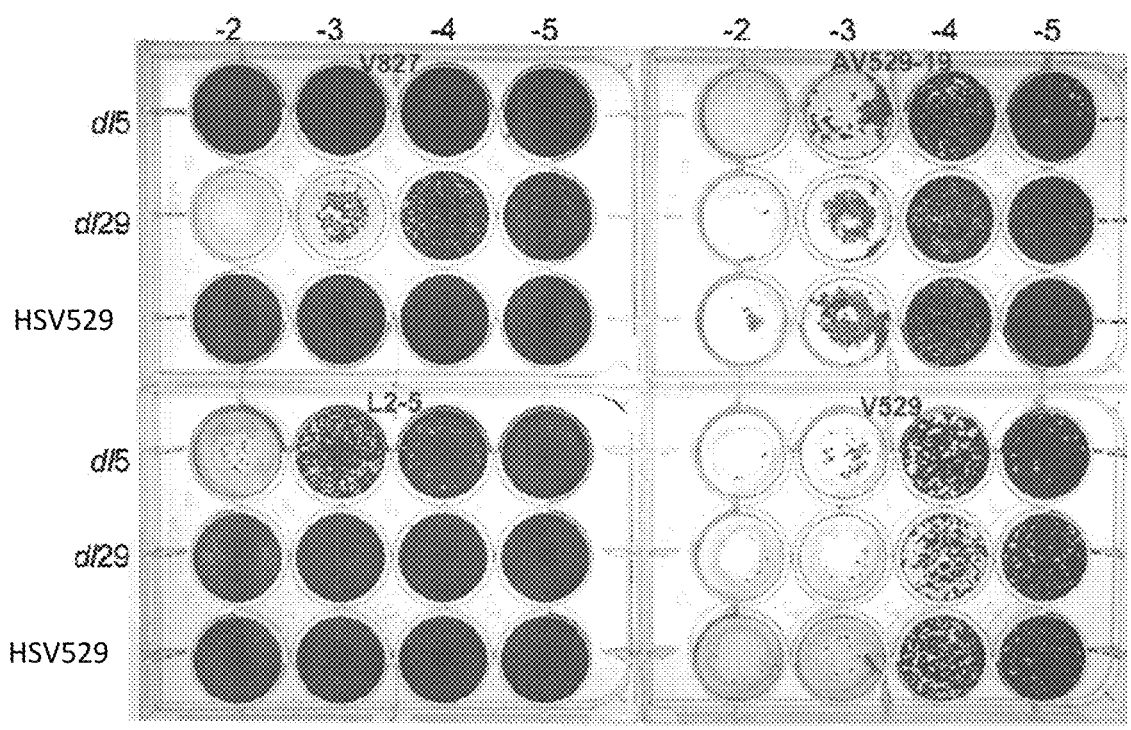
FIG. 1 shows growth of HSV529 when it is added to a monolayer of cells comprising both the UL29 and UL5 complementing genes. The plates on the right side show monolayers of the Vero lines AV529-19 (upper right) and V529 (lower right), both of which express both UL5 and UL29. V827 cells (upper left) express UL29 but not UL5; while L2-5 cells (bottom left) express UL5 but not UL29.

Table 1 provides a listing of certain sequences referenced herein.

TABLE 1

| Description of the Sequences | | |
|---|---|---|
| Description | Sequences | SEQ ID NO |
| Forward primer of 3'UTR sequence of pcDNA3.1 used to transfect AV529-19 | GCCAGCCATCTGTTGTTTGC | 1 |
| Reverse primer of 3'UTR sequence of pcDNA3.1 used to transfect AV529-19 | GGGAGTGGCACCTTCCA | 2 |

TABLE 1-continued

Description of the Sequences

| Description | Sequences | SEQ ID NO |
|---|---|---|
| Probe of 3'UTR sequence of pcDNA3.1 used to transfect AV529-19 | CCCCGTGCCTTCCTT | 3 |
| HSV-1 ICP0 strain 17 | MEPRPGASTR RPEGRPQREP APDVWVFPCD RDLPDSSDSE AETEVGGRGD ADHHDDDSAS EADSTDTELF ETGLLGPQGV DGGAVSGGSP PREEDPGSCG GAPPREDGGS DEGDVCAVCT DEIAPHLRCD TFPCMHRFCI PCMKTWMQLR NTCPLCNAKL VYLIVGVTPS GSFSTIPIVN DPQTRMEAEE AVRAGTAVDF IWTGNQRFAP RYLTLGGHTV RALSPTHPEP TTDEDDDDLD DADYVPPAPR RTPRAPPRRG AAAPPVTGGA SHAAPQPAAA RTAPPSAPIG PHGSSNTNTT TNSSGGGGSR QSRAAAPRGA SGPSGGVGVG VGVVEAEAGR PRGRTGPLVN RPAPLANNRD PIVISDSPPA SPHRPPAAPM PGSAPRPGPP ASAAASGPAR PRAAVAPCVR APPPGPGPRA PAPGAEPAAR PADARRVPQS HSSLAQAANQ EQSLCRARAT VARGSGGPGV EGGHGPSRGA APSGAAPLPS AASVEQEAAV RPRKRRGSGQ ENPSPQSTRP PLAPAGAKRA ATHPPSDSGP GGRGQGGPGT PLTSSAASAS SSSASSSSAP TPAGAASSAA GAASSSASAS SGGAVGALGG RQEETSLGPR AASGPRGPRK CARKTRHAET SGAVPAGGLT RYLPISGVSS VVALSPYVNK TITGDCLPIL DMETGNIGAY VVLVDQTGNM ATRLRAAVPG WSRRTLLPET AGNHVMPPEY PTAPASEWNS LWMTPVGNML FDQGTLVGAL DFRSLRSRHP WSGEQGASTR DEGKQ | 4 |
| HSV-2 ICP0 strain HG52 | MEPRPGTSSR ADPGPERPPR QTPGTQPAAP HAWGMLNDMQ WLASSDSEEE TEVGISDDDL HRDSTSEAGS TDTEMFEAGL MDAATPPARP PAERQGSPTP ADAQGSCGGG PVGEEEAEAG GGGDVCAVCT DEIAPPLRCQ SFPCLHPFCI PCMKTWIPLR NTCPLCNTPV AYLIVGVTAS GSFSTIPIVN DPRTRVEAEA AVRAGTAVDF IWTGNPRTAP RSLSLGGHTV RALSPTPPWP GTDDEDDDLA DVDYVPPAPR RAPRRGGGGA GATRGTSQPA ATRPAPPGAP RSSSSGGAPL RAGVGSGSGG GPAVAAVVPR VASLPPAAGG GRAQARRVGE DAAAAEGRTP PARQPPRAAQE PPIVISDSPP PSPRRPAGPG PLSFVSSSSA QVSSGPGGGG LPQSSGRAAR PRAAVAPRVR SPPRAAAAPV VSASADAAGP APPAVPVDAH RAPRSRMTQA QTDTQAQSLG RAGATDARGS GGPGAEGGPG VPRGTNTPGA APHAAEGAAA RPRKRRGSDS GPAASSSASS SAAPRSPLAP QGVGAKRAAP RRAPDSDSGD RGHGPLAPAS AGAAPPSASP SSQAAVAAAS SSSASSSSAS SSSASSSSAS SSSASSSSAS SSSASSSAGG AGGSVASASG AGERRETSLG PRAAAPRGPR KCARKTRHAE GGPEPGARDP APGLTRYLPI AGVSSVVALA PYVNKTVTGD CLPVLDMETG HIGAYVVLVD QTGNVADLLR AAAPAWSRRT LLPEHARNCV RPPDYPTPPA SEWNSLWMTP VGNMLFDQGT LVGALDFHGL RSRHPWSREQ GAPAPAGDAP AGHGE | 5 |
| BICP0 Bovine herpes virus 1.1 strain Jura | MAPPAAAPEL GSCCICLDAI TGAARALPCL HAFCLACIRR WLEGRPTCPL CKAPVQSLIH SVASDECFEE IPVGGGPGAD GALEPDAAVI WGEDYDAGPI DLTAADGEAS GAGGEAGAAD GSEAGGGAGG AEEAGEARGA GAGRAAGAAG GRAGRGADAA QEFIDRVARG PRLPLLPNTP EHGPGAPYLR RVVEWVEGAL VGSFAVTARE LAAMTDYVMA MLAECGFDDD GLADAMEPLI GEDDAPAFVR SLLFVAARCV TVGPSHLIPQ QSAPPGGRGV VFLDTSDSDS EGSEDDSWSE SEESSSGLST SDLTAIDDTE TEPETDAEVE | 6 |

TABLE 1-continued

Description of the Sequences

| Description | Sequences | SEQ ID NO |
|---|---|---|
| | SRRTRGASGA ARARRPAERQ YVSTRGRQTP | |
| | AVQPAPRSLA RRPCGRAAAV SAPPSSRSRG | |
| | GRRDPRLPAA PRAAPAAQAR ACSPEPREEG | |
| | RGAGLGVAAG ETAGWGAGSE EGRGERRARL | |
| | LGEAGPPRVQ ARRRRRTELD RAPTPAPAPA | |
| | PAPAPISTVI DLTANAPARP ADPAPAAAPG | |
| | PASAGAQIGT PAAAAAVTAA AAAPSVARSS | |
| | APSPAVTAAA TSTAAAISTR APTPSPAGRA | |
| | PAADPRRAGA PALAGAARAE VGRNGNPGRE | |
| | RRPASAMARG DLDPGPESSA QKRRRTEMEV | |
| | AAWVRESLLG TPRRSSAALA PQPGGRQGPS | |
| | LAGLLGRCSG GSAWRQ | |

DESCRIPTION OF THE EMBODIMENTS

ICP0 stimulates recombinant protein expression in a manner that is independent of the promoter used to drive the expression of the recombinant protein. ICP0 may be introduced to a cell comprising a nucleic acid encoding a recombinant protein to increase the expression of the recombinant protein. The nucleic acid may be episomal (encoded on a plasmid) or integrated in the host cell genome. ICP0 may be introduced via transfection or transduction, and may be associated with a constitutive or inducible promoter.

Replication Defective Viral Vaccines

Replication defective viruses are known to those skilled in the art to be a means of developing vaccines, such as those for diseases not amenable to use of inactivated virus or live-attenuated virus vaccines (See T. Dudek and D. M. Knipe Virology 344(1):230-9 (2006)). Replication defective viruses lack one or more functions essential for replication of the viral genome or synthesis and assembly of viral particles. Due to the fact that replication defective viruses do not propagate in normal cells, they can be used as vaccines to present viral antigens and stimulate an immune response. Thus, there is a need to produce high yields of replication defective virus for use in immunizing against certain pathogens.

Encompassed in this invention are methods for producing replication defective virus, such as, for use as vaccines. In one embodiment the replication defective virus is the clinical candidate HSV529. HSV529 is a replication defective virus for prevention of HSV-2 infection. In certain embodiments, the replication defective virus includes those known in the art. Non-limiting examples include members of the herpes family of viruses including, alpha herpes viruses, herpes simplex virus types 1 and 2, and varicella-zoster viruses. This invention is not limited to specific viruses, as the methods for generating a replication defective virus for any particular virus would be understood to those skilled in the art. The methods of producing replication defective virus comprise providing a cell capable of producing a recombinant protein with ICP0, infecting the cell with the replicating defective virus (either after or at the same time as the ICP0), and isolating the replication defective virus. The method may also comprise the further step of purifying the isolated virus.

Similarly, methods for increasing the yield of replication defective viruses, such HSV529 are encompassed, comprising providing a cell capable of producing a recombinant protein with ICP0, infecting the cell with the replicating defective virus (either after or at the same time as the ICP0), and isolating the replication defective virus, wherein the amount of virus isolated is greater than the amount of virus isolated from a control cell system that did not receive ICP0. The method may also comprise the further step of purifying the isolated virus.

Complementary Cells Lines for Production of Replication Defective Viral Vaccines Complementary cell lines for production of replication defective viral vaccines express the missing viral gene product(s) and allow replication of the defective virus (See T. Dudek and D. M. Knipe Virology January 5; 344(1):230-9 (2006)). Replication defective viruses are unable to replicate in normal cells, as one or more steps in viral replication are blocked. In certain embodiments, the complementary cell line can provide the defective viral proteins for propagation to the replication defective virus in trans, such that the specific viral proteins expressed by the complementary cell line can be used by the virus in its replication process to allow propagation of the virus. In one embodiment, AV529-19 is a Vero cell line (ATCC, CCL-81.2), which has been stably transfected to supply the UL5 and ICP8 HSV-2 proteins in trans that are needed for propagation of the HSV529 virus for generation of this vaccine against HSV-2 infection. AV529-19 cells are encompassed in the methods of the invention for use in complementing the replication defective virus HSV529.

Recombinant Proteins

Recombinant proteins are proteins made from DNA sequences that would not otherwise be found in biological organisms. In one embodiment, the recombinant protein is generated from recombinant DNA, wherein the DNA comprises genetic material that is supplied from different sources (e.g., species) or from sequences that have been created that would not otherwise be found in biological organisms. Recombinant proteins may be modified from the natural sequence or may have differences in post-translational modifications. Recombinant proteins may also allow production of protein in cells that would not normally express it or allow production of large quantities of proteins. Recombinant proteins can be viral or non-viral. Non-viral recombinant proteins can be derived from mammalian, plant, insect, or other non-viral protein sources. In certain embodiments, ICP8 or pUL5 may be the recombinant protein that is expressed. In one embodiment, the ICP8 and pUL5 expressed are those of HSV-2. In certain embodiments, the ICP8 and pUL5 are those of HSV-1 or other viruses.

Cells That Can Express Recombinant Proteins

In certain embodiments, cells that can express recombinant proteins include mammalian cells, plant cells, insect cells, yeast cells, bacterial cells, avian cells, and others. In certain embodiments, the cell may be Vero, BHK, CHO, HKB, HEK, NSO, U-2 OS, WI-38, MRC-5, MDCK, FRhL-2, PERC6, and others. Cells capable of expressing recombinant proteins are known to those skilled in the art, and any of these cells are encompassed in this invention. In one embodiment, the cell is AV529-19 and the recombinant protein is ICP8 and pUL5.

Methods of Introducing ICP0

ICP0 can be introduced to a cell comprising a nucleic acid encoding a recombinant protein via any method known to those of skill in the art, such as, for example, by transfection or transduction. The ICP0 nucleic acid may be DNA or RNA. Transfection is a process known to those of skill in the art for introducing nucleic acids into cells. Transfection, as used herein, includes, but is not limited to, lipid transfection, chemical transfection, and physical methods of transfection such as electroporation. In one embodiment, ICP0 is introduced to a cell via transfection. In one embodiment, the transfection is lipid transfection. In another embodiment, the transfection is chemical transfection. In still other embodiments, the transfection is physical transfection, such as, for example, electroporation. The ICP0 nucleic acid sequence may be transfected into a eukaryotic or prokaryotic cell.

In other embodiments, the ICP0 nucleic acid sequence is introduced into the cell comprising DNA capable of expressing a recombinant protein via transduction. Transduction is used herein to comprise introducing DNA into a cell via a viral vector. The term "viral vector" denotes any form of nucleic acid that is derived from a virus and that is used for the transfer of genetic material into a cell via transduction. The term encompasses viral vector nucleic acids, such as DNA and RNA, encapsidated forms of these nucleic acids, and viral particles in which the viral vector nucleic acids have been packaged. The practice of the invention is not constrained by the choice of viral vector, as many forms of viral vectors are known to those skilled in the art. In certain embodiments, the viral vector used for transduction may be retrovirus, lentivirus, adenovirus, adeno-associated virus, or herpesvirus.

Transduction using non-viral vectors is also encompassed. In one embodiment the non-viral vector is Ormosil (organically modified silica or silicate).

The expression vector/construct used in the transduction and transfection methods typically contains a transcription unit or expression cassette with all the elements required for expression of the ICP0 sequence. The particular expression vector that is used to transport the genetic information into the cell may be any conventional vector used by those of skill in the art. Various means may be used to introduce ICP0 nucleic acid sequence into host cells, including the use of calcium phosphate transfection, polybrene, protoplast fusion, electroporation, biolistics, liposomes, microinjection, plasma vectors, viral vectors and any of the other well-known methods for introducing cloned genomic DNA, cDNA, synthetic DNA or other foreign genetic material into a host cell. The selection of vector and method of transfection/transduction is limited only by the need to be capable of successfully introducing ICP0 into the host cell capable of expressing it. The practice of the invention is also not constrained by the choice of promoter in the genetic construct. Plasmids may drive expression of ICP0 using inducible or non-inducible promoters. Inducible promoters may include those controlled by tetracycline, doxycycline, IPTG, or other systems. Non-inducible promoters may include CMV, SV40, CAG, or others.

After the ICP0 is introduced to the cell capable of expressing a recombinant protein, the ICP0 nucleic acid sequence may be incorporated into the genome of the cell (e.g., chromosome, plasmid, plastid, or mitochondrial DNA), converted into an autonomous replicon, or transiently expressed (e.g., transfected mRNA).

In other embodiments, the ICP0 is introduced to a cell capable of expressing a recombinant protein by introducing a virus that naturally expresses ICP0. In one embodiment, ICP0 is introduced by introducing HSV-1, HSV-2, or BHV-1 viruses. HSV-1, HSV-2, and BHV-1 viruses express the ICP0 protein as shown in Sequence IDs 4-6, respectively. In one embodiment, infection of cells capable of expressing a recombinant protein with a virus that encodes ICP0 would lead to increased ICP0 levels. In certain embodiments, the HSV-1, HSV-2, or BHV-1 viruses may be used to introduce ICP0. In one embodiment, replication defective viruses, such as HSV529 or other replication defective HSV-2 viruses, may be used to express ICP0.

In certain embodiments, ICP0 may already be expressed in the cell at the time that a recombinant protein is introduced. In other embodiments, ICP0 is introduced into a cell that does not normally express it.

Methods for Producing Replication Defective Virus In Vitro

In one embodiment, methods for producing, and methods for increasing the yield, of a replication defective virus in vitro are encompassed. In these methods, ICP0 is provided to a cell comprising at least one recombinant protein, wherein the recombinant protein is a protein that is defective in the replication defective virus. A replication defective virus is provided to the cell at the same time as, or after, ICP0. ICP0 increases the expression of the recombinant protein, thereby providing the recombinant protein in trans to the replication defective virus. The replication defective virus is thus capable of replicating, and the in vitro cell system produces and increases the yield of the replication defective virus.

a. Production of HSV-2 Vaccine HSV529

In one exemplary embodiment, the replication defective virus is HSV529. As previously described (See M. C. Bernard et al., PLOS One 10(4):e0121518 (2015)), HSV529 lacks two viral DNA replication genes (UL5 and UL29) and is generated using the complementary helper cell line, AV529-19. AV529-19 is a Vero cell line (ATCC, CCL-81.2), which has been stably transfected to supply the UL5 and ICP8 HSV-2 proteins in trans. Infection of AV529-19 cells by HSV529 can be performed following published protocols (See, S. T. Mundle et al., PLoS One 8, e57224 (2013). Briefly, AV529-19 cells are grown to confluence, and then inoculated with HSV529 at a multiplicity of infection (MOI) of 0.01 in infection medium (40% OptiPro in DPBS with 0.5Xcholesterol, 50 mM sucrose, for example). Infection can proceed over time, such as being allowed to proceed at 34° C. for approximately 72 hr.

In one embodiment, ICP0 is introduced to AV529-19 cells prior to infection with HSV529 in order to increase expression of proteins such as ICP8 and pUL5. In certain embodiments, ICP8 and pUL5 may be those of HSV-2. In other embodiments, ICP8 and pUL5 may come from different sources such as HSV-1 or BHV-1. In certain embodiments, ICP0 can be introduced by transfection. In certain embodiments, ICP0 can be introduced via transduction. In certain embodiments, AV529-19 cells expressing ICP0 can then be infected with HSV529, leading to an increased yield of the viral vaccine. In one embodiment, an increased yield is a yield that quantitatively is an amount of virus obtained following use of AV529-19 cells expressing ICP0 that is greater than the yield following use of control AV529-19 cells that do not express ICP0.

In certain embodiments, ICP0 is introduced at different time points prior to HSV529 infection. In one embodiment ICP0 is introduced 10, 9, 8, 7, 6, 5, 4, 3, 2, 1, 0.5, 0.4, 0.3, 0.2 or 0.1 hours prior to introducing the replication defective virus. In certain embodiments, the MOI of infection and time to harvest are optimized with the protocol including ICP0 introduction to ensure maximal production of HSV529. In certain embodiments, the levels of ICP8 and/or pUL5 are monitored following expression of ICP0 to aid in optimizing the timing of ICP0 introduction.

Various means of viral purification of HSV529 have been described, including ultracentrifugation and sucrose cushion-based purification, as well as chromatography-based purification (See, S. T. Mundle et al., PLoS One 8, e57224 (2013). In some embodiments the replication defective virus produced after ICP0 is introduced is purified, such as by ultracentrifugation or cesium chloride purification. In certain embodiments, mechanical cell disruption or chemical elution of HSV529 from the surface of the infected AV529-19 cells can first be performed, with evidence that chemical elution may allow higher purity viral purification. In one embodiment, purification of the virus may be performed by a combination of dextran sulfate elution followed by Benzonase treatment, depth filtration, anion exchange chromatography, and ultrafiltration/diafiltration. In one embodiment, the virus isolation process follows GMP protocols and produces vaccine preparation to be used for clinical investigation, such as HSV529. In one embodiment, the virus purification process follows GMP protocols and is a prophylactic therapy for infection with HSV-2.

Methods for Increasing Expression of Recombinant Proteins In Vitro

Methods for increasing the expression of recombinant proteins in vitro are encompassed. In one embodiment, the recombinant protein is an antibody or a vaccine antigen. In other embodiments, the recombinant protein is a hormone, enzyme, or other mammalian protein. In other embodiments, the recombinant protein is a peptide used for imaging, diagnostic, or therapeutic purposes. In other embodiments, the recombinant protein is an antibody. Methods for increasing the expression of recombinant proteins in vitro comprise introducing ICP0 to a cell capable of expressing a recombinant protein and isolating the recombinant protein, wherein the recombinant protein is increased in cells introduced with ICP0 as compared to cells that have not been introduced to ICP0.

Herpes Simplex Virus Infected Cell Polypeptide Zero ("ICP0")

The ICP0 of the invention may be any ICP0 from a herpes simplex virus (HSV), including, but not limited to, ICP0 from HSV-1, HSV-2, or BHV-1. In one embodiment an HSV-1 ICP0 is encompassed. In another embodiment, HSV-2 ICP0 is encompassed. In yet other embodiments, bovine BHV-1 ICP0 is encompassed.

In certain embodiments, the ICP0 envisioned is any protein having a RING finger domain, and having ubiquitin ligase activity.

The RING finger domain is known to those of skill in the art and is as described in Barlow, J Mol. Biol. (1994) 237, 201-211 and Boutell and Everett, J. Gen. Virol (2013) 94:465-481 at FIG. 1. The skilled artisan can determine by sequence analysis whether any candidate ICP0 has a RING finger domain.

The skilled artisan can also determine whether any candidate ICP0 has ubiquitin ligase activity, by, for example, conducting a "Ubiquitin Ligase Activity Assay" (see, e.g. Boutell et al (January 2002) J Virology. 76(2):841-50). If a candidate ICP0 exhibits E3 ubiquitin ligase activity in vitro, as evidenced by ubiquitin chain formation, the ICP0 candidate satisfies the "Ubiquitin Ligase Activity Test." Similarly, if a candidate ICP0 lacks ubiquitin ligase activity in vitro, said ICP0 fails to satisfy the "Ubiquitin Ligase Activity Test."

"Ubiquitin Ligase Activity Assay": ICP0, as an E3 ubiquitin ligase, interacts with both E1 and E2 ubiquitination conjugating enzymes to catalyze the formation of poly-ubiquitination chains on substrate proteins. Thus, a Ubiquitin Ligase Activity Assay determines whether a candidate protein can catalyze the formation of poly-ubiquitination chains on substrate proteins in the presence of E1 and E2. A sample activity assay is described below. See, also, detailed methods in Boutell and Davido, Methods (2015) S1046-2023(15):00150-4, and Everett et al. (April 2010) J Virol 84(7):3476-87.

Reaction Mixture Components:
a. E1 ubiquitin-activating enzyme, which can be purified from baculovirus-infected cell extracts or, alternatively, the enzyme can be expressed with an N-terminal polyhistidine tag by a recombinant baculovirus followed by purification from extracts by nickel affinity chromatography. For example, the E1 enzyme can be purified from HeLa cell S100 extracts using ubiquitin affinity chromatography, as described in Boutell 2002, or polyhistidine-tagged E1 enzyme can be expressed and purified by nickel affinity chromatography, as described in Everett 2010.
b. E2 ubiquitination conjugating enzymes can be expressed in recombinant Escherichia coli as a polyhistidine or GST fusion-proteins and purified by nickel or glutathione affinity chromatography. Examples of polyhistidine-tagged UBE2D1 (UbcH5a) have been described in the literature (Boutell 2015; Everett 2010) that can be used in the Ubiquitin Ligase Activity Test.
c. Wild-type ubiquitin (such as from Sigma Aldrich; U6253)

Exemplary Ubiquitin Ligase Activity Test: An example ubiquitination assay is a final reaction volume of 10 µl in 50 mM Tris (pH 7.5), 50 mM NaCl, 1 mM MgCl2, and 5 mM ATP (Sigma-Aldrich; A7699) supplemented with 10 ng E1 and 40 ng of E2 (UBE2D1). To this mixture, 90 ng of candidate purified ICP0 protein is added (Boutell 2015; with a similar reaction described in *Everett* 2010). The reaction is activated by addition of 1 µg of wild-type (Sigma-Aldrich; U6253) or methylated (BostonBiochem; U-501) ubiquitin per reaction and incubated at 37° C. for a time range, for example over 0-90 min. Assays can be terminated by addition of 3× SDS-PAGE loading buffer supplemented with 8M urea and 100 mM dithiothreitol followed by heat denaturation at 95° C. for 10 min, and then SDS-PAGE (12% Bis-Tris NuPAGE; Life Technologies). Following transfer to nitrocellulose membranes, membranes can be blocked in PBS with 10% fetal calf serum for 1 h at room temperature. Blots can then be incubated with anti-ubiquitin antibody (e.g., P4D1 [1/1000]), followed by incubation with appropriate secondary antibodies, based on the preferred quantification analysis system. Quantification of ubiquitination can be performed using these membranes, such as by near-IR imaging using an Odyssey CLx infrared imaging system (LI-COR Biosciences, Boutell 2015) at a resolution of 84 mm or by enhanced chemiluminescence reagent (NEN, Boutell 2002) and exposure to film. Production of polyubiquitin chains can be measured using quantification of the labeled ubiquitin. For example, ubiquitin levels after a 1 h reaction can be measured (Everett 2010) or a time-course of ubiquitin levels over a 90-minute period can be measured (Boutell 2015).

In one embodiment the ICP0 is identical to the amino acids of SEQ ID NO: 4, SEQ ID NO: 5, or SEQ ID NO: 6. The ICP0 may be 99, 98, 97, 96, 95, 94, 93, 92, 91, 90, 85, 84, 83, 82, 81, 80, 79, 78, 77, 76, 75, 74, 73, 72, 71, or 70% identical to any of SEQ ID NO: 4, SEQ ID NO:5, or SEQ ID NO:6, so long as the ICP0 maintains ICP0 activity in the Ubiquitin Ligase Activity Assay.

Stable Cell Lines Expressing ICP0 for Increasing Expression of Recombinant Proteins In one embodiment, methods for generating stable lines expressing ICP0 are encompassed. In certain embodiments, a plasmid containing ICP0 is transfected into a cell line, such as HEK, CHO, HeLa or others, and a stable cell line expressing ICP0 is generated using an appropriate selection method, such as, for example, antibiotic resistance. Clones of the ICP0 stably-transfected line are frozen and then the line is maintained under selection for stable ICP0 expression. In one embodiment, a method for increasing the production of a recombinant protein in the stably-transfected cell is encompassed, comprising maintaining the stably-transfected cell line in culture, and introducing a nucleic acid comprising a recombinant protein, wherein the recombinant protein is expressed at higher levels than in cells that do not comprise ICP0. In another embodiment, a cell line stably-expressing ICP0 line is used to screen for recombinant proteins whose production can be increased by co-expression with ICP0.

Complementary Cell Lines Stably-Expressing ICP0 for Increasing Expression of Replication Defective Viruses In certain embodiments, methods for generating a complementary cell line stably transfected with ICP0 for production of a replication defective viral vaccine is encompassed. In one embodiment, the complementary cell line stably transfected with ICP0 is the AV529-19 cell line, and the replication defective viral vaccine is HSV529. In certain embodiments, stable transfection of ICP0 in the complementary cell system increases the yield of the replication defective virus after infection of the cells compared with the control cell system that does not express ICP0.

EXAMPLES

Example 1

HSV529 Infection of the Cell Line AV529-19 Induces Transcription and Expression of ICP8

The vaccine HSV529 is a replication defective vaccine strain of herpes simplex virus 2 (HSV-2) missing two genes, UL5 and UL29. HSV529 and its complementing cell line AV529-19 have been described previously. See, S. T. Mundle et al., PLoS One 8, e57224 (2013); S. Delagrave et al., PLoS One 7, e46714 (2012).

The UL5 and UL29 genes are necessary for replication of HSV529, and their deletion results in a virus that can deliver viral genomic DNA into human cells and elicit an immune response against the viral proteins, but cannot replicate. The inability to replicate results in a vaccine that is safe to the vaccine recipient. HSV529 can not replicate in partially complementing cells, i.e., HSV529 does not grow if only one of UL5 and UL29 genes are expressed (FIG. 1). HSV529 was not able to grow in either V827 cells (expressing only UL29 and not UL5) or L2-5 cells (expressing only UL5 and not UL29); however, growth was seen in AV529-19 cells which express both complementing genes.

The complementing cell line AV529-19 is a Vero cell line into which HSV-1 orthologs of the two deleted genes, UL5 and UL29, were stably integrated. AV529-19 cells provide HSV529 with the missing proteins pUL5 (helicase encoded by UL5, where 'p' denotes the polypeptide product of the gene UL5) and ICP8, respectively, in trans. See, A. Azizi et al., J Biotechnol 168, 382 (December 2013). Because a CMV promoter drives the expression of UL5 and UL29, it was expected that both genes would be constitutively expressed in AV529-19 cells, and that upon infection with HSV529, the viral vaccine genome would be replicated and new progeny virions comprising the HSV529 genome would be produced by the complementing AV529-19 cells.

Figure 2:
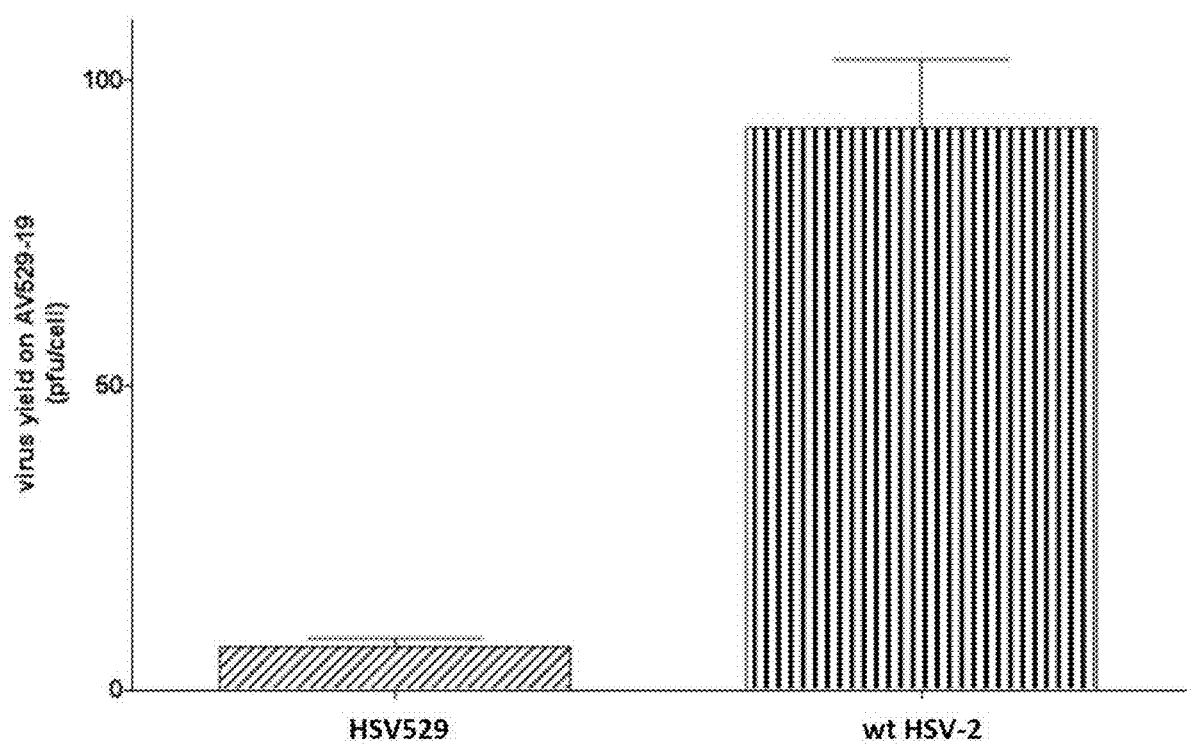
FIG. 2 shows increased replication of wild-type HSV-2 compared to HSV529 in AV529-19 cells. AV529-19 cells were infected with either HSV529 or wild type HSV-2, and infected cells were harvested and lysed. Titers of HSV-2 were then determined by plaque assay on complementing AV529-19 cells. P=0.0173, by 2-tailed t-test.
Figure 3:
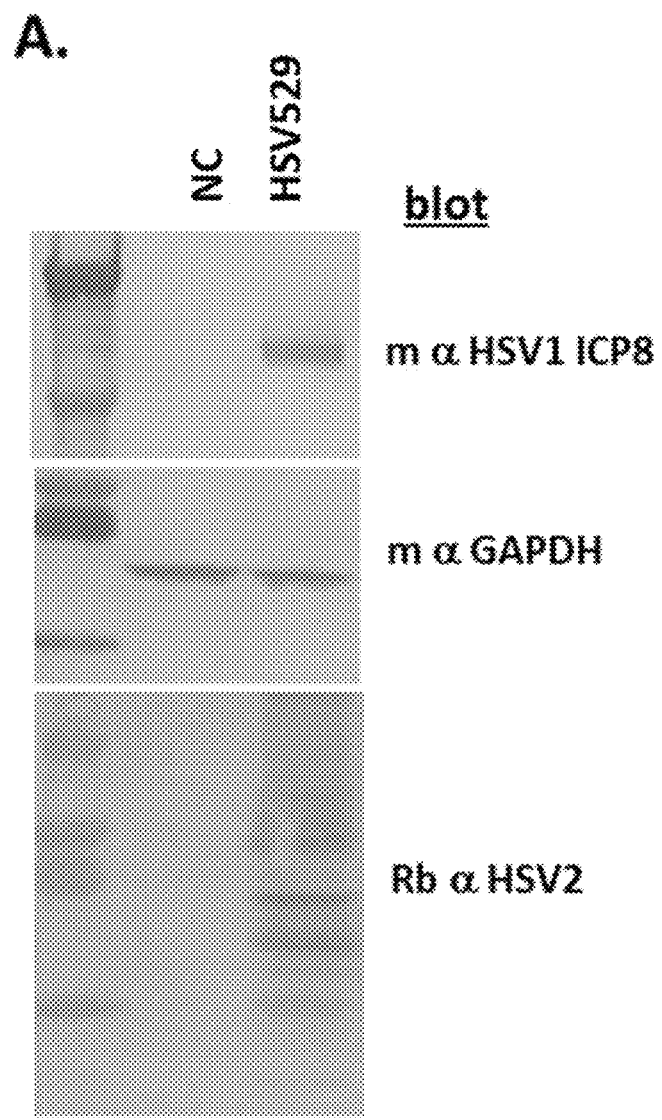
FIG. 3 shows induced expression of ICP8 when AV529-19 cells are infected with HSV529. AV529-19 cells were either mock infected (NC) or infected with HSV529 and then allowed to incubate for 41 hours under standard cell culture conditions. Cells were harvested and lysed in SDS-PAGE sample buffer, and the resulting samples were analyzed by western blotting.

Surprisingly, however, it was observed that complementation of HSV529 in AV529-19 cells yields up to 12-fold less virus per cell than when AV529-19 cells are infected with wild type HSV-2 (FIG. 2). As part of an effort to understand the basis for the imperfect complementation, the expression of ICP8 was studied. Antibodies appropriate for western blot detection of ICP8 were available. Expression of ICP8 was undetectable in uninfected AV529-19 cells, despite being regulated by a constitutive promoter, and despite the clear ability of the cells to complement HSV529 (FIG. 3). Immunodetection with a mouse anti-HSV-1-ICP8 antibody (Abcam, ab20194) indicated that HSV529 infection in AV529-19 cells leads to readily detectable ICP8 expression at 41 hours post-infection (top panel of FIG. 3). No expression of ICP8 was observed in mock-infected (NC) cells. The housekeeping gene product GAPDH was not affected by HSV529 infection (mouse anti-GAPDH; Santa Cruz, sc32233) as shown in middle panel of FIG. 3. Viral protein expression was only seen in infected HSV529 cells using immunodetection with rabbit anti-HSV-2 antibody (Abcam, ab9534) as shown in the bottom blot of FIG. 3.

Figure 4:
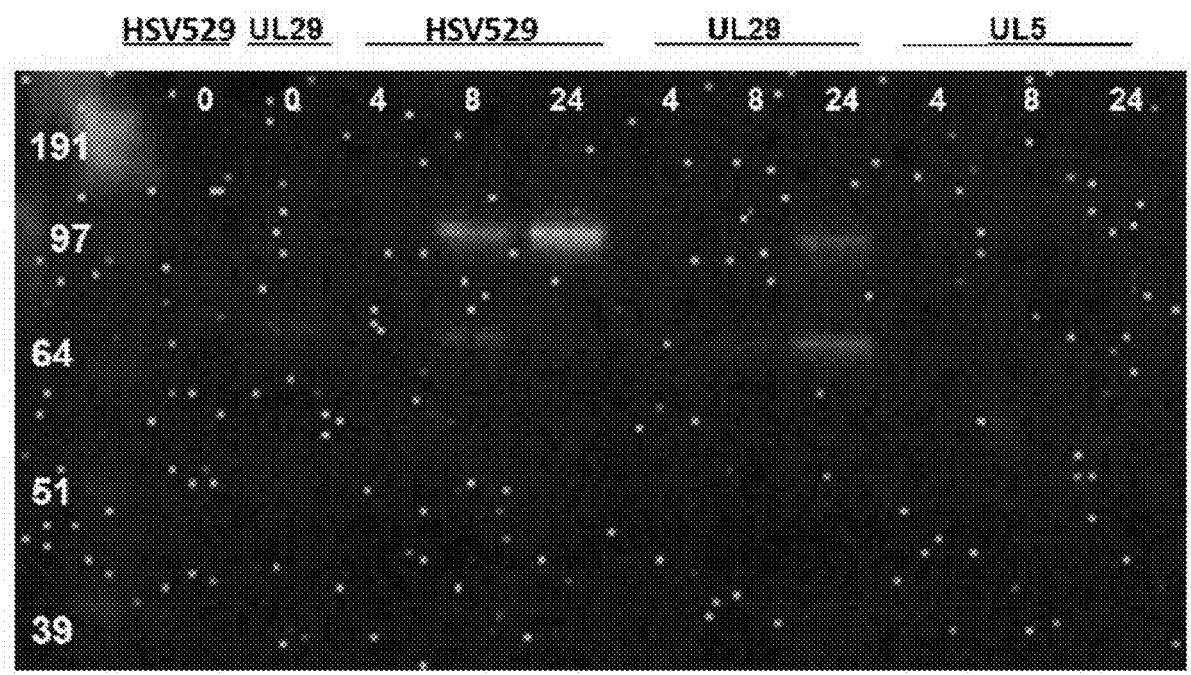
FIG. 4 shows induction of ICP8 expression encoded by a replicon following HSV529 infection. Western blots were performed using chemiluminescence following the induction of ICP8 expression by d15-29 (a.k.a., HSV529) in AV529-19 cells (labeled as AV529) and in Vero cells transfected with a VEE replicon expressing UL29 or UL5. The numbering at the top of the blot indicates hours post-infection; the numbering on the left indicates molecular weight.

We observed that ICP8 could be detected only after cells were infected with HSV529, but not before (FIG. 3 & FIG. 4).

Example 2

HSV529 Infection of the Cell Line AV529-19 Increases Expression of ICP8 Encoded by a Replicon System Using a Venezuelan equine encephalitis (VEE) replicon system, the expression of a replicon-encoded ICP8 in Vero cells after infection with HSV529 was tested (FIG. 4). The UL29 gene was cloned into plasmid p5'VEErep/GFP/Pac, described in Petrakova et al., J Virol 79, 7597 (June 2005), replacing the GFP ORF with the UL29 ORF In the VEE replicons, which is an RNA episome, expression of UL29 or UL5 is driven by the subgenomic VEE promoter encoded by the plasmid p5'VEErep/GFP/Pac Replicon RNA was produced by in vitro transcription of the plasmid driven by an SP6 promoter. The resulting UL29 replicon RNA was transfected into the Vero cells by electroporation using a BioRad Gene Pulser II (320V, 950 μF), and the transfected cells were placed under selection using puromycin (10 μg/mL) to ensure retention of the replicon. A similar replicon encoding UL5 was done in parallel as a control. Cell samples were taken 0, 4, 8 or 24 hours post-infection with HSV529, and tested for ICP8 expression by western blot (FIG. 4). The anti-HSV 1 ICP8 rabbit serum 3-83 was used as a primary antibody and a goat polyclonal anti-rabbit labeled with horseradish peroxidase as a secondary. The SuperSignal West Pico chemiluminescence substrate was used for detection.

ICP8 was not detected at the earliest time points (FIG. 4: 0 h and 4 h time points). Bands of the expected molecular weight (>100 kD) were observed at 24 h for the UL29 replicon cell line, and at both 8 h and 24 h in the AV529-19 cells. As expected, UL5 cells do not produce ICP8 at any time point even with HSV529 infection. Unexpectedly, ICP8 expression was induced when expressed from a replicon. The increased expression of ICP8 appears to be mediated by HSV529 even when ICP8 is expressed from an RNA molecule (the replicon). Therefore, the ability of HSV529 to increase expression of a gene of interest, in this case ICP8, is not dependent on the gene being encoded by DNA.

Example 3

Figure 5:
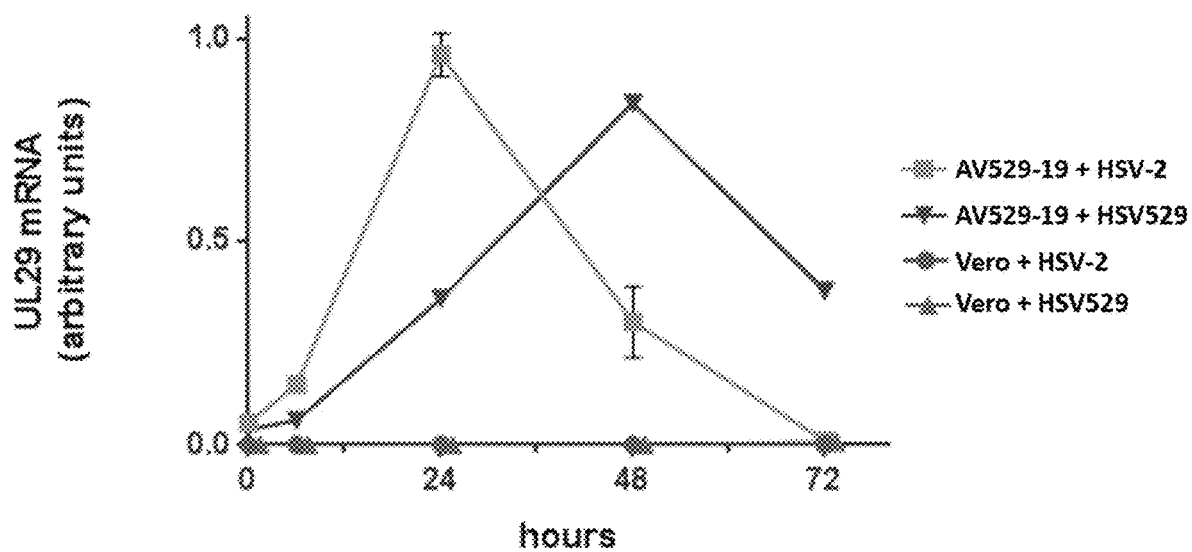
FIG. 5 shows recombinant UL29 mRNA concentrations after infection with HSV-2 or HSV529. Taqman quantitative reverse transcription PCR (qRT-PCR) was used to measure mRNA in either unmodified Vero cells or AV529-19 cells following infection with either HSV-2 (strain 186 syn+1) or HSV529 at 0, 6, 24, 48, and 72 h post-infection. The qRT-PCR primers and probe were specific for the 3' UTR of the pcDNA3.1+vector used to express recombinant UL29 in AV529-19 cells. Error bars show standard deviation.

HSV529 Infection of the Cell Line AV529-19 Increases the Amount of UL29 Transcript in Cells To further our understanding of the increase in ICP8 expression in HSV529-infected cells expressing recombinant UL29, we tested whether a corresponding increase in UL29 mRNA could be detected after infection. A quantitative reverse transcription polymerase chain reaction (qRT-PCR) targeting the 3' untranslated region (UTR) of the recombinant UL29 mRNA using the forward primer SEQ ID1; the reverse primer SEQ ID2; and the probe SEQ ID3; as shown in Table 2 was implemented. The sequence used to generate these primers is exclusively associated with expression of the recombinant UL29 gene. The UL5 gene, for example, is expressed using a different vector having a different 3' UTR and, therefore, will not be targeted. AV529-19 or unmodified Vero cells were infected with either HSV-2 (strain 186 syn+1) or HSV529 (FIG. 5). As expected, unmodified Vero cells had undetectable amounts of recombinant UL29 mRNA at all time points, while AV529-19 had detectable but very low amounts of the recombinant UL29 mRNA at 0 and 6 h post-infection. The mRNA concentration increased by 22- and 26-fold following infection for the HSV529 and HSV-2-infected cells, respectively. UL29 mRNA induction peaked at 24 h post-infection in HSV-2-infected cells and at 48 h post-infection in HSV529-infected cells. These results indicate that the intracellular concentration of the UL29 transcript is increased by infection of cells with either wild-type HSV-2 or HSV529. The kinetics of increased UL29 mRNA expression are consistent with the observed increase in protein levels of ICP8, the UL29 gene product.

Example 4

ICP0 Increases the Expression of ICP8 in the Complementing Cell Line AV529-19

Figure 6:
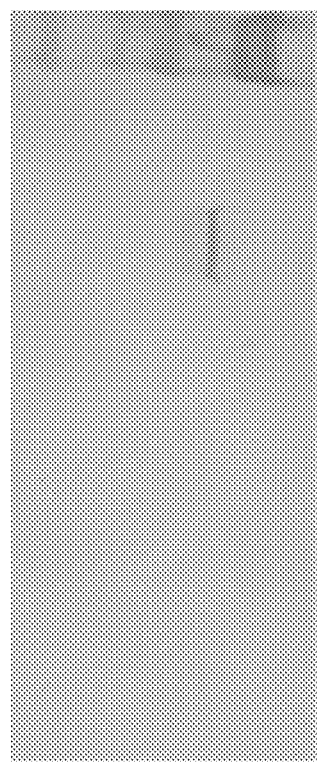
FIG. 6 shows increased expression of ICP8 by transduction of ICP0 in the complementing cell line AV529-19. AV529-19 cells were transduced with the indicated adenovirus vector (MOI=25) and harvested 24 h later.

We hypothesized that an immediate early (IE) protein of HSV-2 might be responsible for the induction of UL29 expression. Therefore, a panel of adenovirus vectors expressing the 5 HSV-2 IE proteins: ICP0, ICP4, ICP22 (C-terminal fragment), ICP27 (combination of N-terminal and C-terminal fragments), and ICP47 were tested. AV529-19 cells were transduced at an MOI of 20 with these various vectors and harvested 24 h later for western blotting using an anti-ICP8 antibody (FIG. 6). A single band showing expression of ICP8 was seen only in the cells transduced with the ICP0-expressing vector. None of the other adenovirus vectors expressing other HSV-s IE proteins showed any effect on ICP8 expression. The 'empty' adenovirus vector itself also caused no expression of ICP8. This result strongly suggests that the induction of ICP8 observed in Examples 1-3 is due to the protein ICP0 expressed by both HSV-2 and HSV529 following infection of AV529-19.

Figure 7:
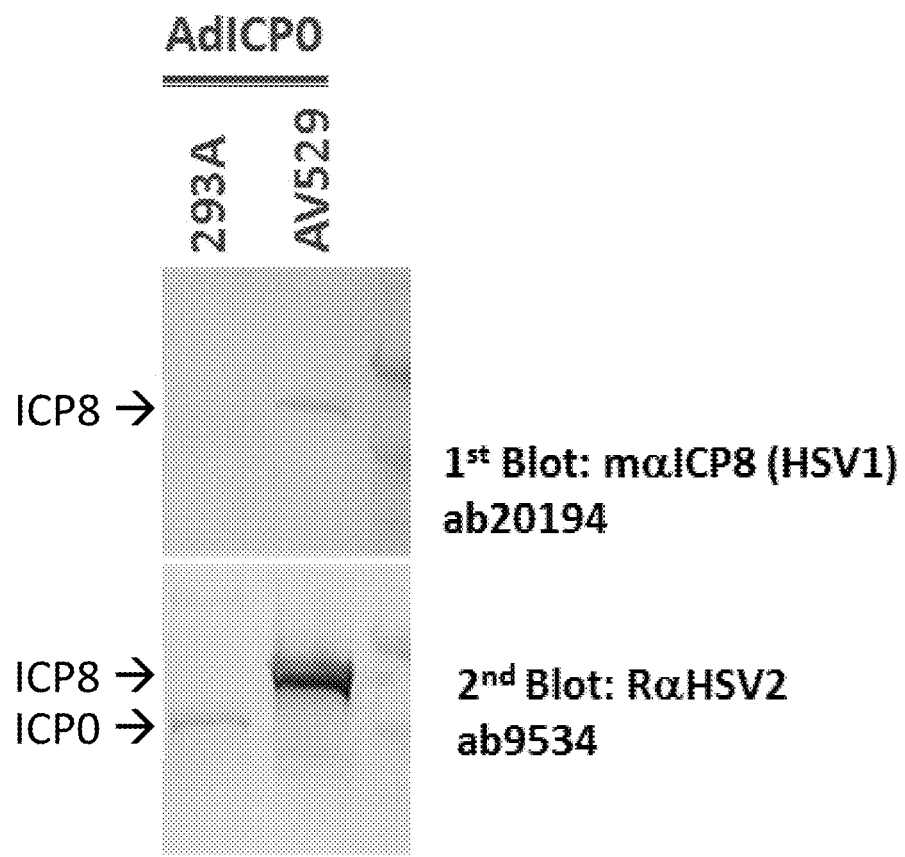
FIG. 7 shows induction of ICP8 by ICP0 infection in AV529-19 cells. The cell line HEK293A, a complementing cell line used to produce adenovirus vectors, and the AV529-19 cell line were infected with an adenovirus vector expressing ICP0. Infected cells were harvested 24 h after infection and analyzed by western blotting.

In a control experiment, transduction of the ICP0-expressing adenovirus resulted in expression of ICP8 in AV529-19 cells, but not in HEK293A cells (FIG. 7). HEK293A cells, a complementing cell line used to produce adenovirus vectors, and the AV529-19 cell line were infected with an adenovirus vector expressing ICP0. Western blot analysis at 24 h after infection indicated that ICP0 is not detectable in AV529-19 cells, presumably because its expression level was below the detection limit of the polyclonal antibody. Immunostaining of the ICP8 band in the AV529-19 cells appeared to have strengthened, which is consistent with the specificity of the polyclonal antibody, while no signal was seen in HEK293A cells. These results indicate that ICP0 expression does not result in ICP8 expression in cells that are not capable of expressing ICP8, such as HEK293A cells.

Example 5

ICP0 Increases the Expression of Episomally-Encoded Recombinant Proteins, as Well as of Proteins of Non-Viral Origin Whether ICP0 could enhance the expression of recombinant proteins other than ICP8 was tested, as was whether this enhancement could be observed using recombinant genes carried on episomal DNA molecules rather than on the host chromosomal DNA. Cells were co-transduced with adenovirus vectors (MOI of 20) expressing various proteins and, 24 hours later, with either an empty adenovirus vector or an adenovirus vector expressing ICP0 (MOI of 20). In this

TABLE 2

Description of the Primers Used for TaqMan Quantification of Recombinant UL29 mRNA

| Target | Description | Forward Primer | Reverse Primer | Probe | Amplicon length |
|--------|-------------|----------------|----------------|-------|-----------------|
| UL29 | 3'UTR sequence of pcDNA3.1 used to transfect AV529-19 | GCCAG CCATC TGTTG TTTGC (SEQ ID NO: 1) | GGGAG TGGCA CCTTCC A (SEQ ID NO: 2) | CCCCG TGCCT TCCTT (SEQ ID NO: 3) | 62 bp | experiment, the recombinant proteins of interest were HSV-2 proteins gD313, VP16, and firefly luciferase. Although AV529-19 cells were used, other cell lines may be used instead (as will be shown in later Examples). Twenty-four hours after co-transduction, infected cells were analyzed on western blots using commercially available antibodies (FIG. 8A and FIG. 8B). Remarkably, in each case, expression of co-transduced proteins was increased by ICP0 but not by the empty adenovirus vector (results for gD shown in FIG. 8A and results for VP16 and firefly luciferase shown in FIG. 8B). These results show that not only is the expression of HSV-2 proteins (ICP8, gD, and VP16) increased by ICP0, but so is the expression of a eukaryotic enzyme (firefly luciferase). Moreover, ICP0 increases expression of episomally-encoded proteins, in addition to the increases of chromosomally-encoded ICP8 shown in earlier Examples.

Figure 9A:
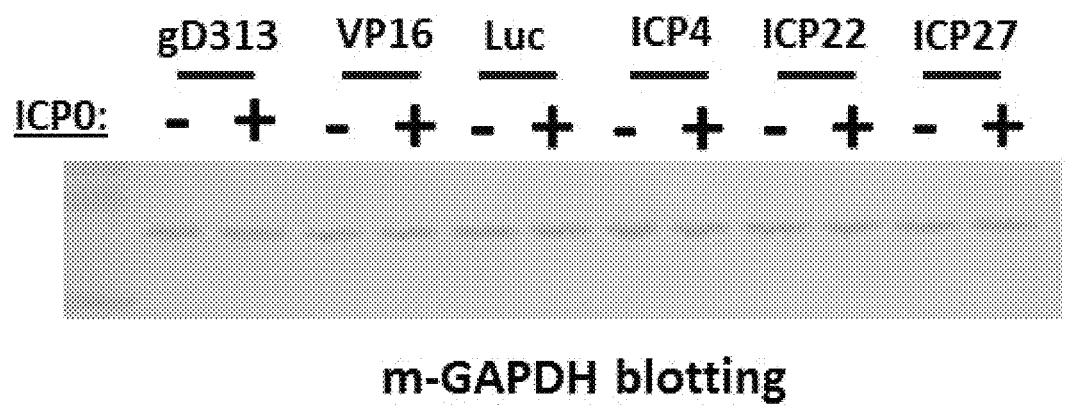
FIGS. 9A and 9B show that ICP0 does not alter host cell protein expression patterns. Cells were co-transduced with the indicated adenovirus vectors and with either an empty vector or with a vector expressing ICP0, as shown respectively by the − or +symbols.
Figure 9B:
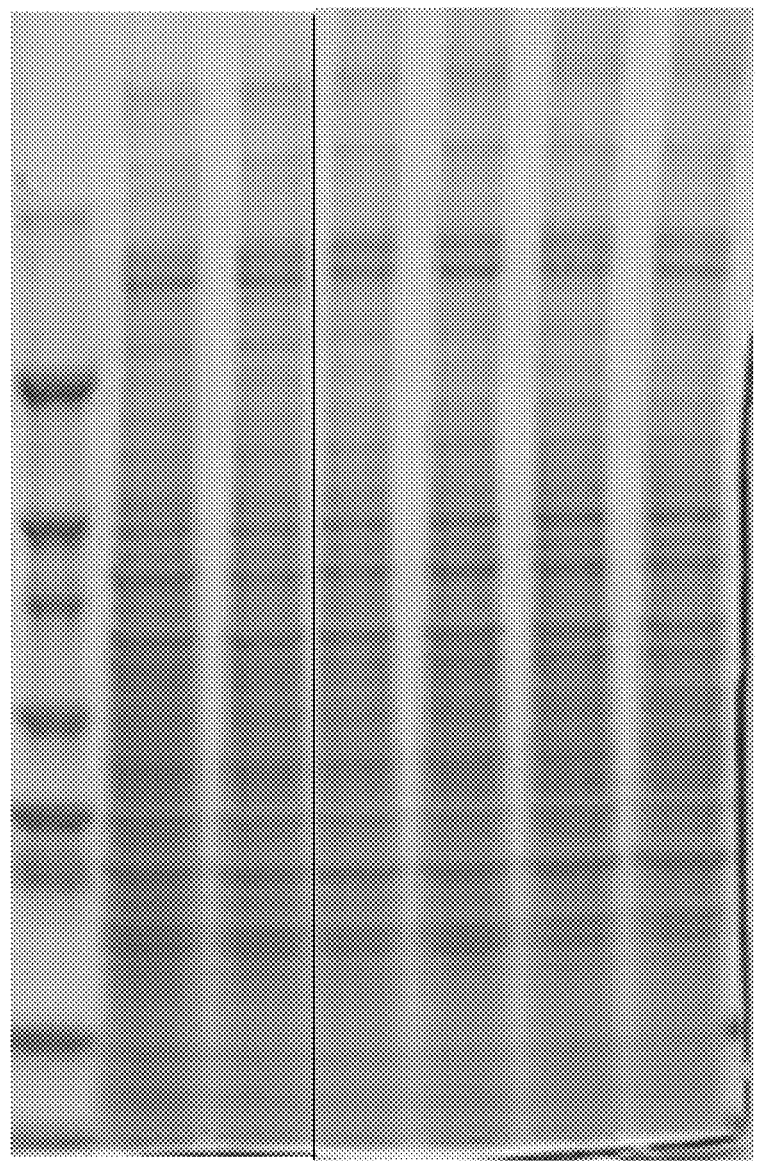

To investigate whether the induced expression of recombinant proteins by ICP0 was specific or due to a global effect on protein expression in the cell, the expression of the housekeeping gene GAPDH was analyzed by western blotting of cells co-transduced with a recombinant protein and with either ICP0 or a negative control adenovirus vector (FIG. 9A). No obvious changes in the expression of this protein were detected as a result of ICP0 expression. We also used SDS-PAGE and Simple-Blue staining analysis of a subset of the same samples for a broader view of protein expression in these cells (FIG. 9B). Negative control (NC) un-transduced cells, empty vector (AdV) cells, and cells co-transduced with gD or VP16 show a similar pattern of bands. Therefore, the effect of ICP0 on protein expression appears to be specific to the recombinant proteins or to a small subset of cellular proteins that includes the recombinant proteins.

Example 6

Figure 10:
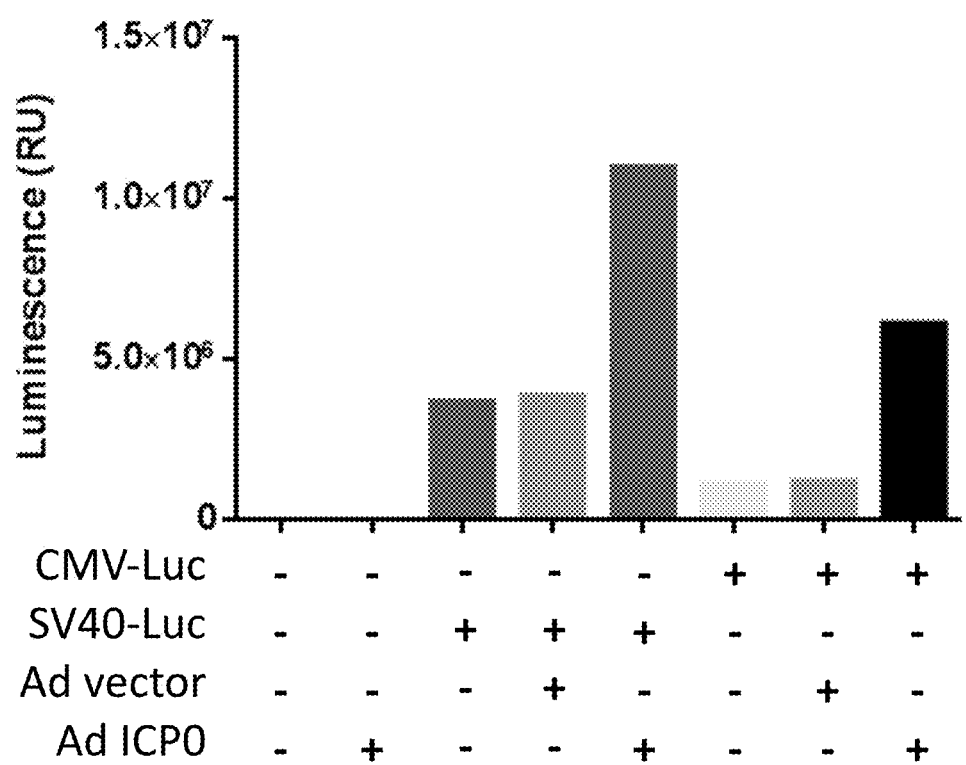
FIG. 10 shows that ICP0 enhances CMV or SV40 promoter-driven expression of plasmid-encoded genes. AV529-19 cells were transiently transfected with plasmids and incubated for 24 h. The plasmids used, pGL4.50 and pGL4.13 (Promega), encode firefly luciferase under the control of the CMV and the SV40 promoter, respectively. The transfected cells were then transduced with a control adenovirus vector or a vector expressing ICP0. Cells were harvested 36 h later and analyzed by luminescence assay.

ICP0 Increases the Expression of Recombinant Proteins Encoded by Different Plasmids and Using Different Promoters In the above Examples, the recombinant proteins were encoded by a stably integrated CMV promoter-driven transgene (ICP8) or by an adenovirus vector that also drives expression using the CMV promoter. We therefore tested the ability of ICP0 to increase the expression of a recombinant protein encoded by two different plasmids driving the expression of the transgene with either the CMV promoter or the SV40 promoter. ICP0 transduction increased expression of firefly luciferase by 2.8-fold and 5.1-fold for plasmids with the SV40 and CMV promoters, respectively, compared with control vector transduction (FIG. 10). Therefore, ICP0-mediated enhancement of recombinant, plasmid-borne gene expression is independent of the promoter used.

Figure 11:
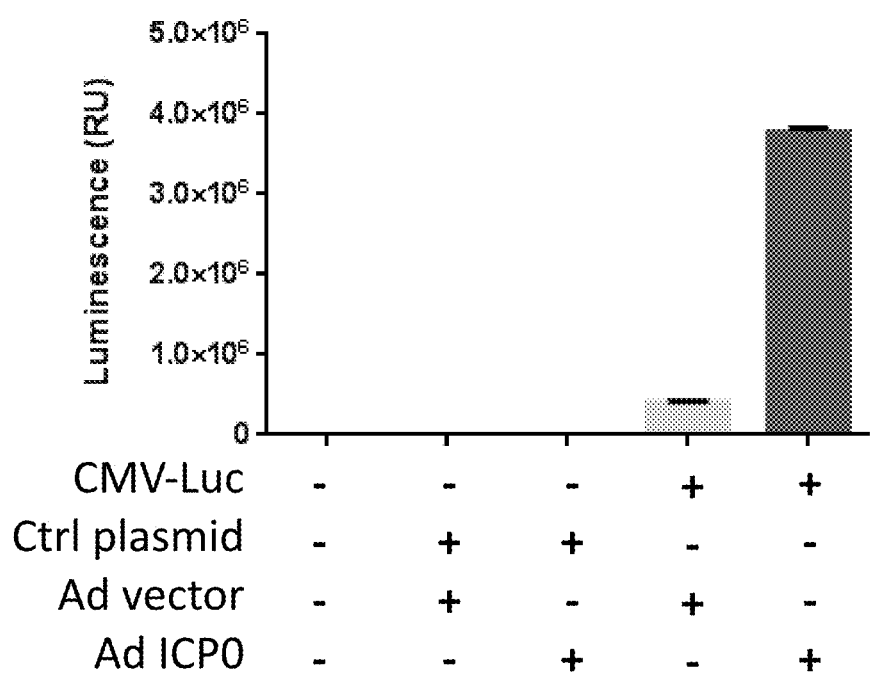
FIG. 11 shows enhanced expression of plasmid-encoded genes in Vero cells induced by ICP0. Vero cells were transiently transfected with plasmids and allowed to recover for 24 h. These plasmids encoded either no transgene (Ctrl plasmid) or firefly luciferase under the control of the CMV promoter (CMV-Luc). The cells were then transduced with a control adenovirus (Ad) vector or a vector expressing ICP0 (Ad ICP0). Cells were harvested 36 h later and analyzed by luminescence assay. $P<0.0001$ for the difference between control adenovirus vector and adenovirus expressing ICP0; error bars show one standard deviation.

The data shown in FIG. 10 were obtained using AV529-19 cells. As stated above, these are Vero cells engineered with chromosomally integrated copies of the genes UL29 and UL5. To show that UL29 and UL5 are not necessary for the observed effect of ICP0, we reproduced part of the experiment using Vero cells (FIG. 11). As seen in FIG. 11, ICP0 transduction produced a 9-fold increase in luciferase expression in Vero cells, confirming that the enhancing effect of ICP0 can be achieved without expression of UL29 or UL5. The difference between control adenovirus vector and vector expressing ICP0 was extremely statistically significant by ANOVA analysis ($P<0.0001$).

Figure 12:
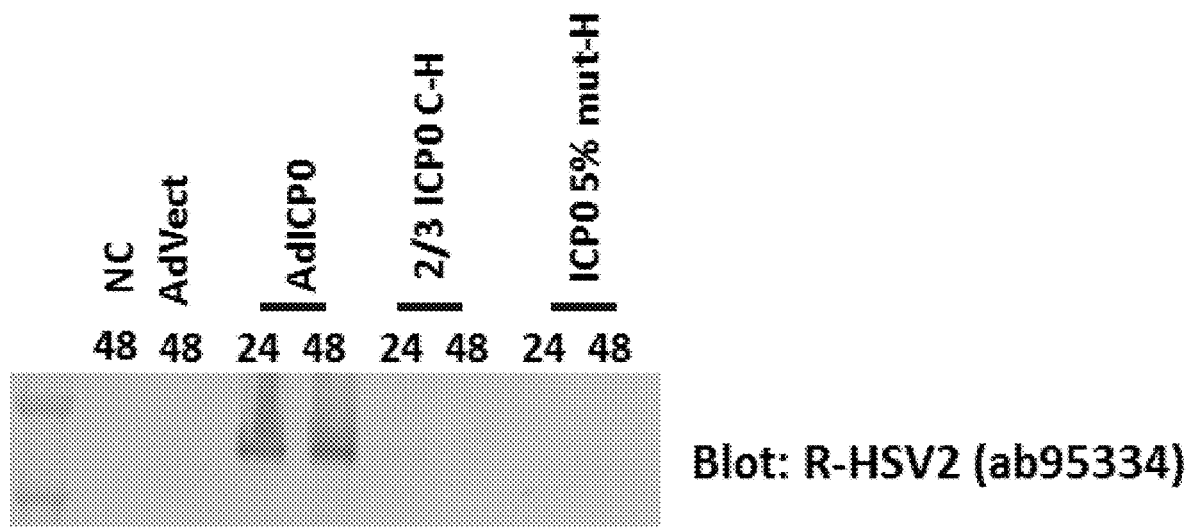
FIG. 12 indicates that non-conservative ICP0 mutants do not induce ICP8 expression in AV529-19 cells. AV529-19 cells were transduced with adenovirus vectors comprising no foreign gene (AdVect), wild type ICP0 (AdICP0), a mutant of ICP0 in which the N-terminal approximately ⅓ is deleted and the C-terminus is labeled with a poly-histidine tag (⅔ ICP0 C-H), or a mutant of ICP0 in which approximately 5% of all amino acids have non-conservative substitutions and a C-terminal poly-histidine tag (ICP0 5% mut-H). Non-transduced cells (NC) were also included as negative controls. Following either 48 or 24 h of incubation post-transduction, as indicated, cells were harvested and analyzed by western blotting with a rabbit polyclonal anti-HSV-2 antibody.

To confirm that the ICP0 polypeptide is responsible for the enhanced expression effect, the ability of two different ICP0 mutants to induce ICP8 expression was assessed. Wild-type and mutant ICP0 were delivered to AV529-19 cells via an adenovirus vector. Western blotting with a rabbit polyclonal anti-HSV-2 antibody that cross-reacts with HSV-1 ICP8 clearly shows the expression of ICP8 in wild-type ICP0-treated cells, but not in cells treated with a version of ICP0 in which the N-terminal ⅓ was deleted (⅔ ICP0 C-H construct), or another version in which about 5% of amino acids in the protein are substituted (ICP0 5% mut-H) (FIG. 12). Therefore, the ICP0 polypeptide sequence must be mostly preserved to increase expression of ICP8 in AV529-18 cells.

Example 7

Figure 13:
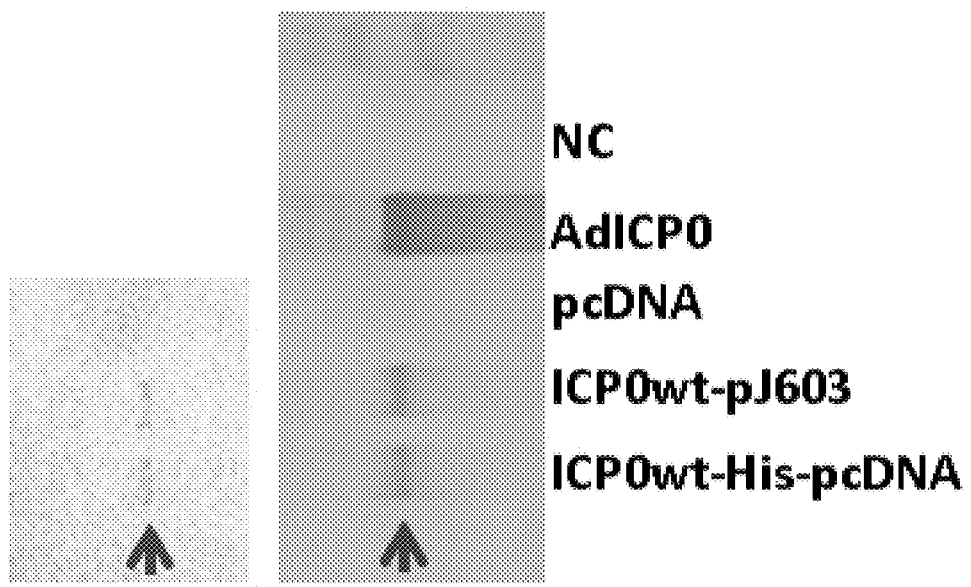
FIG. 13 shows that plasmid transfection of ICP0 increases recombinant protein expression in AV529-19 cells. AV529-19 cells were either not transfected (NC), transduced with an adenovirus expressing ICP0 (AdICP0), transfected with the empty vector pcDNA3.1 (pcDNA), transfected with ICP0 expressed from the plasmid pJ603 (ICP0wt-pJ603), or transfected with ICP0 with a C-terminal poly-histidine tag (ICP0wt-His-pcDNA). Forty-two hours post-transfection, cells were harvested and analyzed by western blotting. The top blot was probed with the rabbit anti-HSV-2 polyclonal antibody, which cross-reacts with HSV-1 ICP8 (arrow), while the lower blot used the same samples and was probed with a mouse anti-HSV-1 ICP8 monoclonal antibody (arrow).

ICP0 Increases Recombinant Protein Expression when it is Provided to Cells Via a Plasmid In the above Examples, ICP0 was expressed using either HSV-2, HSV529, or an adenovirus vector. We therefore tested the ability of ICP0 expressed from a plasmid to increase protein expression. AV529-19 cells were transiently transfected with an empty plasmid or with ICP0 expressed from a CMV promoter in two different plasmids (pcDNA3.1 and pj603), and then levels of expression of ICP8 were measured by western blot. Expression of ICP8 was clearly induced by ICP0 transfection by either plasmid in cells harvested 42 h post-transfection (FIG. 13). The top blot of FIG. 13 was probed with the rabbit anti-HSV-2 polyclonal antibody which cross-reacts with HSV-1 ICP8 (red arrow). Induction of ICP8 was clearly detected in the AdICP0 lane as well as in cells transfected with ICP0 expressed from a plasmid. To confirm the identity of ICP8 in the cells, another western blot was carried out with the same samples and probed with a mouse anti-HSV-1 ICP8 monoclonal antibody and showed similar results (lower blot of FIG. 13). The ICP0 expressed from pcDNA3.1 bears a C-terminal poly-histidine tag, and this tag did not hinder ICP8 induction. Control samples, either with no transfection (NC) or in which an empty vector (pcDNA) was transfected, showed no ICP8 expression.

Figure 14:
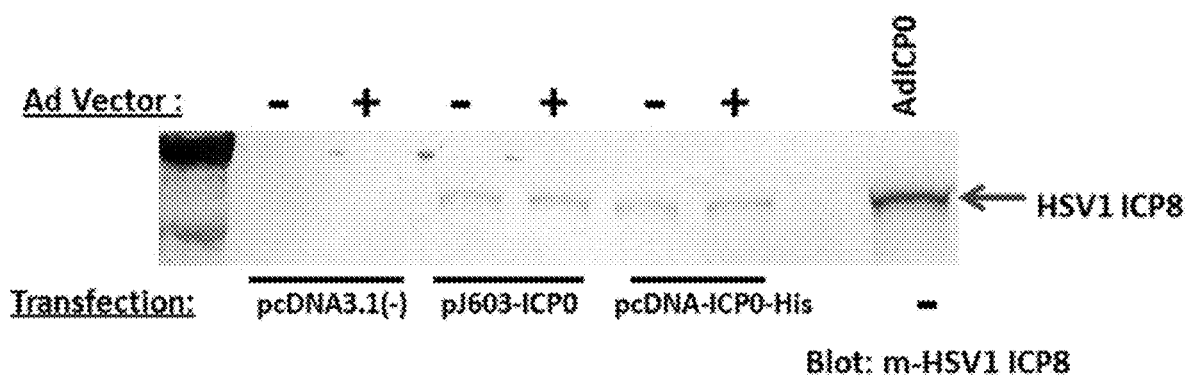
FIG. 14 shows that the adenovirus vector itself does not contribute to the ICP0-mediated enhanced expression effect. AV529-19 cells were transfected with the indicated plasmids, and 24 h later either transduced with an adenovirus vector (+) or not transduced (−). Control cells were left untransfected and later transduced with adenovirus expressing ICP0 (Ad ICP0). Samples were harvested 36 h post-transduction, and western blotting analysis of the cells was carried out using an anti-HSV-1-ICP8 mouse monoclonal antibody.

While transfection of plasmids containing ICP0 DNA was clearly capable of inducing ICP8, this induction was weaker than that which was mediated by transduction with an adenovirus vector expressing ICP0 (FIG. 13). We hypothesized that the lower efficiency of transient transfection compared to adenovirus-mediated transduction may explain this observation. To rule out the possibility that adenovirus components had increased the efficiency of the ICP0 enhancement, we transfected AV529-19 cells with ICP0 plasmids and 24 hours later transduced the transfected cells with 'empty' adenovirus vector. Cells were then assayed 36 h later for ICP8 protein expression. Adenovirus vector transduction following plasmid transfection did not enhance ICP8 protein expression (FIG. 14). These results suggest that lower ICP0 plasmid transfection efficiency limited the enhancement in protein expression for cells transfected with plasmid compared to cells transduced with adenovirus.

Example 8

ICP0 Increases the Yield of HSV529

As discussed in Examples 1 and 3, HSV-2 replicated more efficiently in AV529-19 cells than does HSV529 (FIG. 2).

Figure 15:
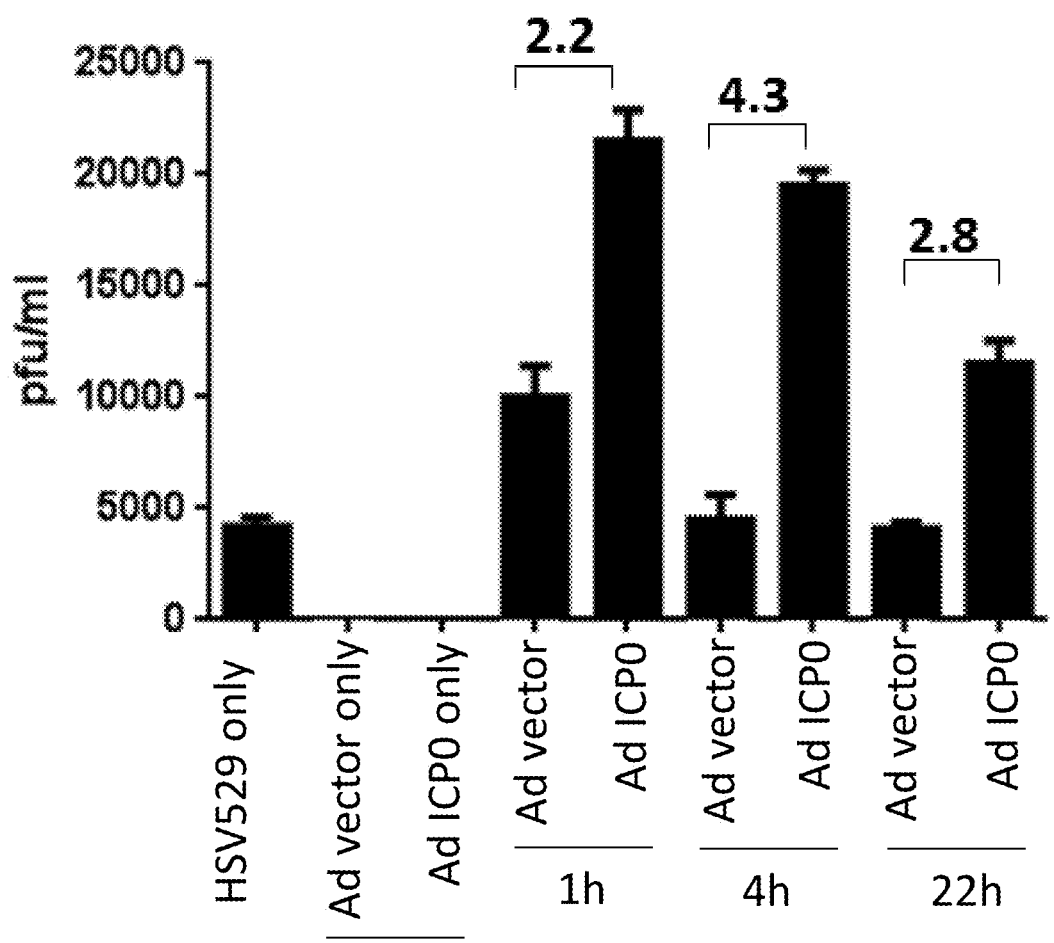
FIG. 15 shows that ICP0 transduction increases the yield of HSV529 in AV529-19 cells. AV529-19 cells were transduced with an empty adenovirus vector (Ad vector) or an adenovirus vector expressing ICP0 (Ad ICP0) and were infected with HSV529 either 1 h, 4 h, or 22 h later. One sample of control cells was not infected with adenovirus (HSV529 only), providing a baseline for HSV529 yield. Other samples were transduced with Ad vector or Ad ICP0 4 h prior to a mock infection instead of being infected with HSV529. Cells were harvested 24 h after infection or mock infection with HSV529, and lysate was analyzed by plaque assay to quantify production of HSV529.

The data also indicated that HSV529 infection causes a slower and slightly lower increase in the expression of the recombinant UL29 transcript compared to HSV-2 (FIG. 5). Given this correlation between ICP8 expression and viral yields, we hypothesized that AV529-19 cells expressing ICP0 prior to infection with HSV529 would induce ICP8 expression and would therefore complement the virus more efficiently and produce higher yields when infected with HSV529. Transduction of AV529-19 with adenovirus vector expressing ICP0 before infection with HSV529 showed a clear increase in HSV529 yields compared to transduction with an empty adenovirus vector (FIG. 15). Transduction with ICP0 was carried out at 1 h, 4 h, or 22 h prior to HSV529 infection and, compared to the yields obtained with empty vector, resulted in increases of 2.8-, 4.3-, and 2.2-fold, respectively. Compared to a baseline, un-transduced sample of HSV529-infected cells (HSV529 only), the greatest enhancement in yield (5.5-fold) was achieved by infection of HSV529 at 1 h following transduction of adenovirus expressing ICP0. Thus, appropriately timed expression of recombinant ICP0 can trigger increased production of the vaccine HSV529 in AV529-19 cells.

Example 9

Inducible Expression of ICP8

Figure 16:
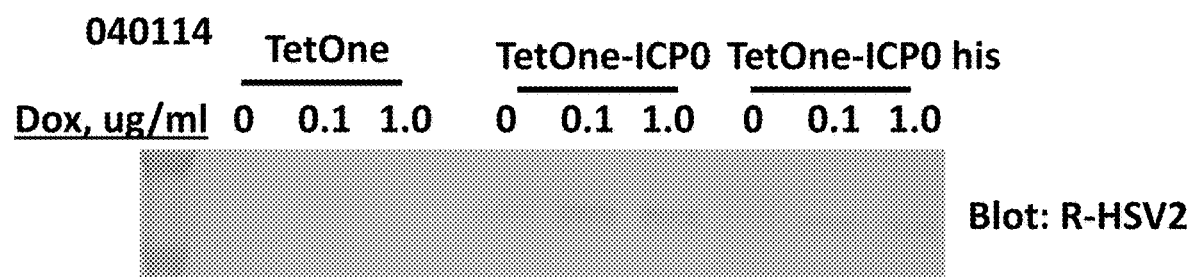
FIG. 16 shows induction of ICP8 expression by doxycycline using a doxycycline-sensitive vector to express ICP0. AV529 cells were transfected with the pTetOne vector (Clontech), or engineered versions of the plasmid which express ICP0 (TetOne-ICP0) or an ICP0 to which is appended a polyhistidine tag at the carboxyl terminus (TetOne-ICP0 his). Transfected cells were incubated in the presence of 0, 0.1, or 1 µg/mL of doxycycline, harvested, lysed, and analyzed by western blotting using an anti-HSV-2 polyclonal rabbit antibody that detects ICP8.

Whether it is possible to induce the expression of ICP8 in AV529 cells using a small molecule compound was tested. The TetOne vector was used to construct a plasmid that expresses ICP0 under the control of a doxycycline-sensitive promoter (TetOne-ICP0). This plasmid was transfected into the AV529 cell line. Increasing the concentration of doxycycline in the culture medium of transfected cells induced the expression of the protein ICP8, which is encoded by the stably inserted UL29 gene in this line (FIG. 16). Similar results were seen for an engineered version of the plasmid to which a polyhistidine tag was appended at the carboxyl terminus (TetOne-ICP0 his). Control AV529 cells transfected with an empty TetOne vector did not show increased expression of ICP8. Therefore, these data show that ICP8 expression can be induced, by a mechanism of induced expression of ICP0, using a small molecule drug.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method of increasing heterologous recombinant protein expression from a viral promoter in vitro, comprising:

introducing by transfection a herpes simplex virus (HSV) infected cell polypeptide zero (ICP0) to a cell comprising a transgene encoding the heterologous protein operably linked to the viral promoter, wherein the cell is a mammalian cell and is capable of expressing the recombinant protein from the viral promoter; and isolating the recombinant protein from the cell, wherein:
(i) the recombinant protein is non-viral; and/or
(ii) the ICP0 is introduced by transfection with a plasmid comprising a sequence encoding ICP0 operably linked to a CMV promoter, an SV40 promoter, or a non-inducible promoter comprising a TATA box, GC-box, CCAAT box, B recognition element, and an initiator element; the heterologous recombinant protein is heterologous relative to the cell; and the heterologous protein is expressed by 24 hours after introduction of ICP0.

2. The method of claim 1, wherein the recombinant protein is an antibody, a vaccine antigen, a hormone, or an enzyme.

3. The method of claim 1, wherein the recombinant protein is a mammalian protein.

4. The method of claim 1, wherein the recombinant protein is non-viral.

5. The method of claim 1, wherein the ICP0 is introduced by transfection with a plasmid encoding ICP0 and comprising a non-inducible promoter, and the non-inducible promoter is a CMV promoter, an SV40 promoter, or a promoter comprising a TATA box, GC-box, CCAAT box, B recognition element, and an initiator element.

6. The method of claim 1, wherein the cell is a Vero, BHK, CHO, HKB, HEK, NSO and U-2 OS, WI-38, MRC-5, MDCK, FRhL-2, or PERC6 cell.

7. The method of claim 1, wherein the cell is a Vero cell.

* * * * *

UNITED STATES PATENT AND TRADEMARK OFFICE
CERTIFICATE OF CORRECTION

PATENT NO. : 11,286,465 B2
APPLICATION NO. : 16/230990
DATED : March 29, 2022
INVENTOR(S) : Simon Delagrave et al.

Page 1 of 1

It is certified that error appears in the above-identified patent and that said Letters Patent is hereby corrected as shown below:

On the Title Page

In the name of the Applicant, item (71):
"Sanofi Pasteur Biologies, LLC" should read --Sanofi Pasteur Biologics, LLC--.

Signed and Sealed this
Fifth Day of August, 2025

Coke Morgan Stewart
*Acting Director of the United States Patent and Trademark Office*

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Forward primer of 3'UTR sequence of pcDNA3.1
      used to transfect AV529-19

<400> SEQUENCE: 1
gccagccatc tgttgtttgc                                               20

<210> SEQ ID NO 2
<211> LENGTH: 17
<212> TYPE: DNA
<213> ORGANISM: Artificial Sequence
<220> FEATURE:
<223> OTHER INFORMATION: Reverse primer of 3'UTR sequence of pcDNA3.1
      used to transfect AV529-19

<400> SEQUENCE: 2
gggagtggca ccttcca                                                  17

<210> SEQ ID NO 3
<211> LENGTH: 15
<212> TYPE: DNA
<213> ORGANISM: Artificial Sequence
<220> FEATURE:
<223> OTHER INFORMATION: Probe of 3'UTR sequence of pcDNA3.1 used to
      transfect AV529-19
```

<400> SEQUENCE: 3
ccccgtgcct tcctt                                                          15

<210> SEQ ID NO 4
<211> LENGTH: 775
<212> TYPE: PRT
<213> ORGANISM: Human herpesvirus 1 strain 17

<400> SEQUENCE: 4

Met Glu Pro Arg Pro Gly Ala Ser Thr Arg Arg Pro Glu Gly Arg Pro
1               5                   10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Ser Ala Ser Glu Ala Asp Ser
    50                  55                  60

Thr Asp Thr Glu Leu Phe Glu Thr Gly Leu Leu Gly Pro Gln Gly Val
65                  70                  75                  80

Asp Gly Gly Ala Val Ser Gly Gly Ser Pro Pro Arg Glu Glu Asp Pro
                85                  90                  95

Gly Ser Cys Gly Gly Ala Pro Pro Arg Glu Asp Gly Gly Ser Asp Glu
            100                 105                 110

Gly Asp Val Cys Ala Val Cys Thr Asp Glu Ile Ala Pro His Leu Arg
        115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175

Pro Ile Val Asn Asp Pro Gln Thr Arg Met Glu Ala Glu Glu Ala Val
            180                 185                 190

Arg Ala Gly Thr Ala Val Asp Phe Ile Trp Thr Gly Asn Gln Arg Phe
        195                 200                 205

Ala Pro Arg Tyr Leu Thr Leu Gly Gly His Thr Val Arg Ala Leu Ser
    210                 215                 220

Pro Thr His Pro Glu Pro Thr Thr Asp Glu Asp Asp Asp Leu Asp
225                 230                 235                 240

Asp Ala Asp Tyr Val Pro Pro Ala Pro Arg Arg Thr Pro Arg Ala Pro
                245                 250                 255

Pro Arg Arg Gly Ala Ala Ala Pro Pro Val Thr Gly Gly Ala Ser His
            260                 265                 270

Ala Ala Pro Gln Pro Ala Ala Ala Arg Thr Ala Pro Pro Ser Ala Pro
        275                 280                 285

Ile Gly Pro His Gly Ser Ser Asn Thr Asn Thr Thr Asn Ser Ser
    290                 295                 300

Gly Gly Gly Gly Ser Arg Gln Ser Arg Ala Ala Ala Pro Arg Gly Ala
305                 310                 315                 320

Ser Gly Pro Ser Gly Gly Val Gly Val Gly Val Gly Val Glu Ala
                325                 330                 335

Glu Ala Gly Arg Pro Arg Gly Arg Thr Gly Pro Leu Val Asn Arg Pro
            340                 345                 350

Ala Pro Leu Ala Asn Asn Arg Asp Pro Ile Val Ile Ser Asp Ser Pro

```
                355                 360                 365
Pro Ala Ser Pro His Arg Pro Ala Ala Pro Met Pro Gly Ser Ala
    370                 375                 380
Pro Arg Pro Gly Pro Pro Ala Ser Ala Ala Ser Gly Pro Ala Arg
385                 390                 395                 400
Pro Arg Ala Ala Val Ala Pro Cys Val Arg Ala Pro Pro Gly Pro
                405                 410                 415
Gly Pro Arg Ala Pro Ala Pro Gly Ala Glu Pro Ala Ala Arg Pro Ala
                420                 425                 430
Asp Ala Arg Arg Val Pro Gln Ser His Ser Ser Leu Ala Gln Ala Ala
                435                 440                 445
Asn Gln Glu Gln Ser Leu Cys Arg Ala Arg Ala Thr Val Ala Arg Gly
    450                 455                 460
Ser Gly Gly Pro Gly Val Glu Gly Gly His Gly Pro Ser Arg Gly Ala
465                 470                 475                 480
Ala Pro Ser Gly Ala Ala Pro Leu Pro Ser Ala Ser Val Glu Gln
                485                 490                 495
Glu Ala Ala Val Arg Pro Arg Lys Arg Gly Ser Gly Gln Glu Asn
                500                 505                 510
Pro Ser Pro Gln Ser Thr Arg Pro Leu Ala Pro Gly Ala Lys
    515                 520                 525
Arg Ala Ala Thr His Pro Pro Ser Asp Ser Gly Pro Gly Gly Arg Gly
    530                 535                 540
Gln Gly Gly Pro Gly Thr Pro Leu Thr Ser Ser Ala Ala Ser Ala Ser
545                 550                 555                 560
Ser Ser Ser Ala Ser Ser Ser Ala Pro Thr Pro Ala Gly Ala Ala
                565                 570                 575
Ser Ser Ala Ala Gly Ala Ala Ser Ser Ala Ser Ala Ser Ser Gly
                580                 585                 590
Gly Ala Val Gly Ala Leu Gly Gly Arg Gln Glu Glu Thr Ser Leu Gly
                595                 600                 605
Pro Arg Ala Ala Ser Gly Pro Arg Gly Pro Arg Lys Cys Ala Arg Lys
    610                 615                 620
Thr Arg His Ala Glu Thr Ser Gly Ala Val Pro Ala Gly Gly Leu Thr
625                 630                 635                 640
Arg Tyr Leu Pro Ile Ser Gly Val Ser Ser Val Val Ala Leu Ser Pro
                645                 650                 655
Tyr Val Asn Lys Thr Ile Thr Gly Asp Cys Leu Pro Ile Leu Asp Met
                660                 665                 670
Glu Thr Gly Asn Ile Gly Ala Tyr Val Val Leu Val Asp Gln Thr Gly
                675                 680                 685
Asn Met Ala Thr Arg Leu Arg Ala Ala Val Pro Gly Trp Ser Arg Arg
    690                 695                 700
Thr Leu Leu Pro Glu Thr Ala Gly Asn His Val Met Pro Pro Glu Tyr
705                 710                 715                 720
Pro Thr Ala Pro Ala Ser Glu Trp Asn Ser Leu Trp Met Thr Pro Val
                725                 730                 735
Gly Asn Met Leu Phe Asp Gln Gly Thr Leu Val Gly Ala Leu Asp Phe
                740                 745                 750
Arg Ser Leu Arg Ser Arg His Pro Trp Ser Gly Glu Gln Gly Ala Ser
    755                 760                 765
Thr Arg Asp Glu Gly Lys Gln
    770                 775
```

<210> SEQ ID NO 5
<211> LENGTH: 825
<212> TYPE: PRT
<213> ORGANISM: Human herpesvirus 2 strain HG52

<400> SEQUENCE: 5

```
Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
    50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Pro Ala Glu Arg Gln Gly
                85                  90                  95

Ser Pro Thr Pro Ala Asp Ala Gln Gly Ser Cys Gly Gly Gly Pro Val
            100                 105                 110

Gly Glu Glu Glu Ala Glu Ala Gly Gly Gly Asp Val Cys Ala Val
        115                 120                 125

Cys Thr Asp Glu Ile Ala Pro Pro Leu Arg Cys Gln Ser Phe Pro Cys
130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
            180                 185                 190

Arg Thr Arg Val Glu Ala Glu Ala Ala Val Arg Ala Gly Thr Ala Val
        195                 200                 205

Asp Phe Ile Trp Thr Gly Asn Pro Arg Thr Ala Pro Arg Ser Leu Ser
    210                 215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Gly Gly Gly Ala Gly Ala
            260                 265                 270

Thr Arg Gly Thr Ser Gln Pro Ala Ala Thr Arg Pro Ala Pro Pro Gly
        275                 280                 285

Ala Pro Arg Ser Ser Ser Ser Gly Gly Ala Pro Leu Arg Ala Gly Val
    290                 295                 300

Gly Ser Gly Ser Gly Gly Gly Pro Ala Val Ala Ala Val Val Pro Arg
305                 310                 315                 320

Val Ala Ser Leu Pro Pro Ala Ala Gly Gly Arg Ala Gln Ala Arg
                325                 330                 335

Arg Val Gly Glu Asp Ala Ala Ala Glu Gly Arg Thr Pro Pro Ala
            340                 345                 350

Arg Gln Pro Arg Ala Ala Gln Glu Pro Pro Ile Val Ile Ser Asp Ser
        355                 360                 365

Pro Pro Pro Ser Pro Arg Arg Pro Ala Gly Pro Gly Pro Leu Ser Phe
```

```
            370                 375                 380
Val Ser Ser Ser Ala Gln Val Ser Gly Pro Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Arg Ala Ala Ala Pro Val Val Ser
            420                 425                 430

Ala Ser Ala Asp Ala Ala Gly Pro Ala Pro Ala Val Pro Val Asp
                435                 440                 445

Ala His Arg Ala Pro Arg Ser Arg Met Thr Gln Ala Gln Thr Asp Thr
            450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Gly Pro Gly Val Pro Arg Gly Thr Asn
                485                 490                 495

Thr Pro Gly Ala Ala Pro His Ala Ala Glu Gly Ala Ala Arg Pro
            500                 505                 510

Arg Lys Arg Arg Gly Ser Asp Ser Gly Pro Ala Ala Ser Ser Ser Ala
            515                 520                 525

Ser Ser Ser Ala Ala Pro Arg Ser Pro Leu Ala Pro Gln Gly Val Gly
        530                 535                 540

Ala Lys Arg Ala Ala Pro Arg Ala Pro Asp Ser Asp Ser Gly Asp
545                 550                 555                 560

Arg Gly His Gly Pro Leu Ala Pro Ala Ser Ala Gly Ala Ala Pro Pro
                565                 570                 575

Ser Ala Ser Pro Ser Ser Gln Ala Ala Val Ala Ala Ala Ser Ser Ser
            580                 585                 590

Ser Ala Ser Ser Ser Ala Ser Ser Ser Ala Ser Ser Ser Ser
        595                 600                 605

Ala Ser Ser Ser Ala Ser Ser Ser Ala Ser Ser Ser Ala
            610                 615                 620

Ser Ser Ser Ala Gly Gly Ala Gly Gly Ser Val Ala Ser Ala Ser Gly
625                 630                 635                 640

Ala Gly Glu Arg Arg Glu Thr Ser Leu Gly Pro Arg Ala Ala Pro
                645                 650                 655

Arg Gly Pro Arg Lys Cys Ala Arg Lys Thr Arg His Ala Glu Gly Gly
            660                 665                 670

Pro Glu Pro Gly Ala Arg Asp Pro Ala Pro Gly Leu Thr Arg Tyr Leu
            675                 680                 685

Pro Ile Ala Gly Val Ser Ser Val Val Ala Leu Ala Pro Tyr Val Asn
        690                 695                 700

Lys Thr Val Thr Gly Asp Cys Leu Pro Val Leu Asp Met Glu Thr Gly
705                 710                 715                 720

His Ile Gly Ala Tyr Val Val Leu Val Asp Gln Thr Gly Asn Val Ala
                725                 730                 735

Asp Leu Leu Arg Ala Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
        755                 760                 765

Pro Ala Ser Glu Trp Asn Ser Leu Trp Met Thr Pro Val Gly Asn Met
        770                 775                 780

Leu Phe Asp Gln Gly Thr Leu Val Gly Ala Leu Asp Phe His Gly Leu
785                 790                 795                 800
```

```
Arg Ser Arg His Pro Trp Ser Arg Glu Gln Gly Ala Pro Ala Pro Ala
            805                 810                 815

Gly Asp Ala Pro Ala Gly His Gly Glu
            820                 825

<210> SEQ ID NO 6
<211> LENGTH: 676
<212> TYPE: PRT
<213> ORGANISM: Infectious bovine rhinotracheitis virus

<400> SEQUENCE: 6

Met Ala Pro Pro Ala Ala Pro Glu Leu Gly Ser Cys Cys Ile Cys
1               5                   10                  15

Leu Asp Ala Ile Thr Gly Ala Ala Arg Ala Leu Pro Cys Leu His Ala
                20                  25                  30

Phe Cys Leu Ala Cys Ile Arg Arg Trp Leu Glu Gly Arg Pro Thr Cys
            35                  40                  45

Pro Leu Cys Lys Ala Pro Val Gln Ser Leu Ile His Ser Val Ala Ser
        50                  55                  60

Asp Glu Cys Phe Glu Glu Ile Pro Val Gly Gly Pro Gly Ala Asp
65                  70                  75                  80

Gly Ala Leu Glu Pro Asp Ala Ala Val Ile Trp Gly Glu Asp Tyr Asp
                85                  90                  95

Ala Gly Pro Ile Asp Leu Thr Ala Ala Asp Gly Glu Ala Ser Gly Ala
            100                 105                 110

Gly Gly Glu Ala Gly Ala Ala Asp Gly Ser Glu Ala Gly Gly Gly Ala
        115                 120                 125

Gly Gly Ala Glu Glu Ala Gly Glu Ala Arg Gly Ala Gly Ala Gly Arg
    130                 135                 140

Ala Ala Gly Ala Ala Gly Gly Arg Ala Gly Arg Gly Ala Asp Ala Ala
145                 150                 155                 160

Gln Glu Phe Ile Asp Arg Val Ala Arg Gly Pro Arg Leu Pro Leu Leu
                165                 170                 175

Pro Asn Thr Pro Glu His Gly Pro Gly Ala Pro Tyr Leu Arg Arg Val
            180                 185                 190

Val Glu Trp Val Glu Gly Ala Leu Val Gly Ser Phe Ala Val Thr Ala
        195                 200                 205

Arg Glu Leu Ala Ala Met Thr Asp Tyr Val Met Ala Met Leu Ala Glu
    210                 215                 220

Cys Gly Phe Asp Asp Asp Gly Leu Ala Asp Ala Met Glu Pro Leu Ile
225                 230                 235                 240

Gly Glu Asp Asp Ala Pro Ala Phe Val Arg Ser Leu Leu Phe Val Ala
                245                 250                 255

Ala Arg Cys Val Thr Val Gly Pro Ser His Leu Ile Pro Gln Gln Ser
            260                 265                 270

Ala Pro Pro Gly Gly Arg Gly Val Val Phe Leu Asp Thr Ser Asp Ser
        275                 280                 285

Asp Ser Glu Gly Ser Glu Asp Asp Ser Trp Ser Glu Ser Glu Glu Ser
    290                 295                 300

Ser Ser Gly Leu Ser Thr Ser Asp Leu Thr Ala Ile Asp Asp Thr Glu
305                 310                 315                 320

Thr Glu Pro Glu Thr Asp Ala Glu Val Glu Ser Arg Arg Thr Arg Gly
                325                 330                 335

Ala Ser Gly Ala Ala Arg Ala Arg Arg Pro Ala Glu Arg Gln Tyr Val
```

```
                   340                 345                 350
Ser Thr Arg Gly Arg Gln Thr Pro Ala Val Gln Pro Ala Pro Arg Ser
        355                 360                 365

Leu Ala Arg Arg Pro Cys Gly Arg Ala Ala Val Ser Ala Pro Pro
        370                 375                 380

Ser Ser Arg Ser Arg Gly Gly Arg Arg Asp Pro Arg Leu Pro Ala Ala
385                 390                 395                 400

Pro Arg Ala Ala Pro Ala Ala Gln Ala Arg Ala Cys Ser Pro Glu Pro
                405                 410                 415

Arg Glu Glu Gly Arg Gly Ala Gly Leu Gly Val Ala Ala Gly Glu Thr
                420                 425                 430

Ala Gly Trp Gly Ala Gly Ser Glu Glu Gly Arg Gly Glu Arg Arg Ala
        435                 440                 445

Arg Leu Leu Gly Glu Ala Gly Pro Pro Arg Val Gln Ala Arg Arg Arg
        450                 455                 460

Arg Arg Thr Glu Leu Asp Arg Ala Pro Thr Pro Ala Pro Ala Pro Ala
465                 470                 475                 480

Pro Ala Pro Ala Pro Ile Ser Thr Val Ile Asp Leu Thr Ala Asn Ala
                485                 490                 495

Pro Ala Arg Pro Ala Asp Pro Ala Pro Ala Ala Ala Pro Gly Pro Ala
                500                 505                 510

Ser Ala Gly Ala Gln Ile Gly Thr Pro Ala Ala Ala Ala Val Thr
        515                 520                 525

Ala Ala Ala Ala Ala Pro Ser Val Ala Arg Ser Ser Ala Pro Ser Pro
        530                 535                 540

Ala Val Thr Ala Ala Thr Ser Thr Ala Ala Ala Ile Ser Thr Arg
545                 550                 555                 560

Ala Pro Thr Pro Ser Pro Ala Gly Arg Ala Pro Ala Ala Asp Pro Arg
                565                 570                 575

Arg Ala Gly Ala Pro Ala Leu Ala Gly Ala Ala Arg Ala Glu Val Gly
                580                 585                 590

Arg Asn Gly Asn Pro Gly Arg Glu Arg Arg Pro Ala Ser Ala Met Ala
        595                 600                 605

Arg Gly Asp Leu Asp Pro Gly Pro Glu Ser Ser Ala Gln Lys Arg Arg
        610                 615                 620

Arg Thr Glu Met Glu Val Ala Ala Trp Val Arg Glu Ser Leu Leu Gly
625                 630                 635                 640

Thr Pro Arg Arg Ser Ser Ala Ala Leu Ala Pro Gln Pro Gly Gly Arg
                645                 650                 655

Gln Gly Pro Ser Leu Ala Gly Leu Leu Gly Arg Cys Ser Gly Gly Ser
                660                 665                 670

Ala Trp Arg Gln
        675
```